(12) United States Patent
Ezban et al.

(10) Patent No.: US 7,829,529 B2
(45) Date of Patent: Nov. 9, 2010

(54) USE OF FACTOR VIIA OR A TISSUE FACTOR ANTAGONIST FOR REGULATING GENE EXPRESSION AND CELL MIGRATION OR CHEMOTAXIS

(75) Inventors: Mirella Ezban, Copenhagen O (DK); Lars Christian Petersen, Horsholm (DK); Agneta Siegbahn, Uppsala (SE)

(73) Assignee: Novo Nordisk Health Care A/G, Zurich (CH)

( * ) Notice: Subject to any disclaimer, the term of this patent is extended or adjusted under 35 U.S.C. 154(b) by 165 days.

(21) Appl. No.: 12/178,126

(22) Filed: Jul. 23, 2008

(65) Prior Publication Data

US 2009/0036378 A1     Feb. 5, 2009

Related U.S. Application Data

(63) Continuation of application No. 11/152,468, filed on Jun. 14, 2005, now abandoned, which is a continuation of application No. 10/051,044, filed on Jan. 14, 2002, now abandoned, which is a continuation of application No. PCT/DK00/00401, filed on Jul. 14, 2000.

(60) Provisional application No. 60/148,300, filed on Aug. 11, 1999.

(30) Foreign Application Priority Data

Jul. 14, 1999   (DK)   ............... 1999 01023
Aug. 12, 1999   (DK)   ............... 1999 01117

(51) Int. Cl.
    *C07K 14/00*     (2006.01)
(52) U.S. Cl. .......................................... 514/2; 530/350
(58) Field of Classification Search ................... None
    See application file for complete search history.

(56) References Cited

U.S. PATENT DOCUMENTS

2005/0245449 A1   7/2005   Kongsbak et al.

FOREIGN PATENT DOCUMENTS

| WO | WO 93/06855 | 4/1993 |
|---|---|---|
| WO | WO 97/33995 | 9/1997 |
| WO | WO 98/58661 | 12/1998 |
| WO | WO 99/03498 | 1/1999 |
| WO | WO 99/66031 | 12/1999 |
| WO | WO 02/077218 | 10/2002 |
| WO | WO 02087605 | 11/2002 |
| WO | WO 03007983 | 1/2003 |
| WO | WO 03039581 | 5/2003 |
| WO | WO 03039582 | 5/2003 |
| WO | WO 03039584 | 5/2003 |
| WO | WO 03039590 | 5/2003 |

OTHER PUBLICATIONS

U.S. Appl. No. 11/579,680, filed Nov. 7, 2006, Johannson et al.
Sato et al., "Tissue factor pathway inhibitor inhibits aortic smooth muscle cell migration induced by tissue factor/factor VIIa complex," Thrombosis Haemostasis, vol. 97, pp. 1138-1141 (1997).
Taniguchi et al., "Enhanced Expression of Urokinase Receptor Induced through the Tissue Factor VIIa Pathway in Huma Pancreatic Cancer", (1998) Cancer Res., vol. 58, pp. 4461-4467.
Pendurthi et al., "Binding of Factor VIIa to Tissue Factor Induces Alterations in Gene Expression in Human Fibroblast Cells: Up-regulation of Poly(A) Polymerase," (1997) Proc. Natl. Acad. Sci., vol. 94, pp. 12598-12603.
Camerer et al., "Coagulation Factors VIIa and Xa Induce Cell Signaling Leading to Up-regulation or the erg-1 Gene," (1999) J Biol. Chem., vol. 274, No. 45, pp. 32225-32233.
Pendurthi et al., "Factor VIIa and Thrombin Induce the Expression of Cyr61 and Connective Tissue Growth Factor," (2000) J. Biol. Chem., vol. 275, No. 19, pp. 14632-14641.
Ollivier, J.C. et al., "Vascular Endothelial Growth Factor Production by Fibroblasts in Response to Factor VIIa Binding to Tissue Factor Involves Thrombin and Factor Xa," Arteriosclerosis, Thrombosis, and Vascular Biology, 2000, vol. 20, pp. 1374-1381.
Ollivier et al., "Tissue Factor-Dependent Vascular Endothelial Growth Factor Production by Human Fibroblasts in Response to Activated Factor VII," (1998) Blood, vol. 91, No. 8, pp. 2698-2703.
Niemi et al., "Haemostatis Disturbances in Burned Patients During Early Excision and Skin Grafting," (1998) Blood Coag. Fibrinol., vol. 9, pp. 19-28.
Cunningham et al., "Tissue Factor and Factor VIIa Receptor/Ligand Interactions Induce Proinflammatory Effects in Macrophages," (1999) Blood, vol. 94, No. 10, pp. 3413-3420.
Borgognone et al., "The Role of Antithrombin III and Factor VII in the Prognosis and Treatment of Burn Injury," (1969) The Italian Journal of Plastic Surgery, vol. 21, pp. 459-464.

(Continued)

*Primary Examiner*—Karen Cochrane Carlson
(74) *Attorney, Agent, or Firm*—Reza Green; Teresa Chen

(57) ABSTRACT

The present invention relates to use of FVII and/or FVIIa and/or another TF agonist and/or FVIIai and/or another TF antagonist in therapeutic treatment of pathological conditions that can be related to cell migration or treated by specific regulation of cell migration or chemotaxis.

3 Claims, 18 Drawing Sheets

OTHER PUBLICATIONS

Figure 1A:
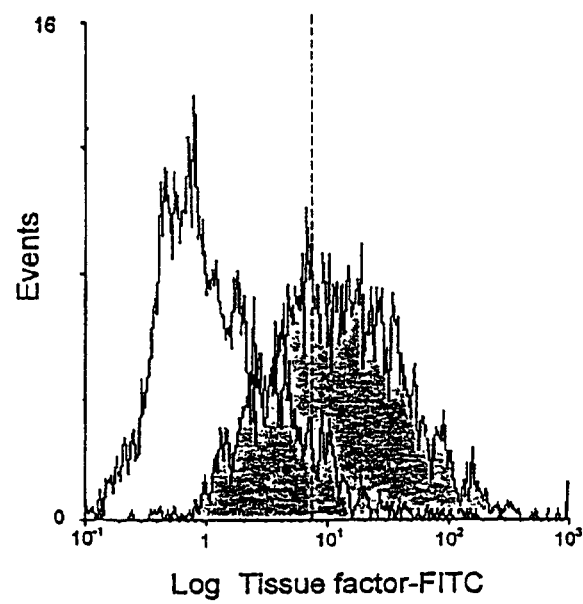

Dincer et al., "Human Recombinant Activated Factor Seven, Novoseven (rVIIa), in the Management of Massive Bleeding Despite Adequate Resuscitation in Major Trauma," Disorders of Coagulation or Fibrinolysis, Abstract# 3918, p. 110b.

Ingerslev, J. et al., "Home Treatment with Recombinant Activated Factor VII: Results from One Centre," (1998) Blood Coagulation or Fibronolysis, vol. 9 (Suppl 1), pp. S107-S110.

Petrini P. et al., "Treatment of Acute Bleeds with Recombinant Activated Factor VII During Immune Tolerance Therapy," (1998) Blood Coagulation or Fibrinolysis, vol. 9 (Suppl 1), pp. S143-S146.

Aggarwal, A. et al., 43rd Annual Meeting of the Society of Hematology, Part 2, Dec. 7-11, 2001.

Aggarwal, A. et al., Use of recombinant Activated Factor VII (rFV11a) in the Management of Intractable Bleeding in Surgical and Trauma Patients. Blood. vol. 98(11). p. 66B (2001).

Aitken, M.G., Recombinant factor VIIa, Emergency Medicine Australasia, vol. 16, pp. 446-455 (2004).

Alcorn, K. et al., Single Institution Experience of Recombinant Activated Factor VII (Novo-Seven) in the Management of Intractable Bleeding in Surgical and Trauma Patients, Blood, vol. 100(11), p. 3840 (2002).

Aldouri, M., The Use of Recombinant Factor VIIa in Controlling Surgical Bleeding in Non-Haemophiliac Patients, Pathophysiology of Haemostasis and Thrombosis, vol. 32(Suppl1), pp. 141-146 (2002).

Argall, J., Factor VIIa for intractable blood loss in trauma, Emergency Medical Journal, vol. 19. pp. 556-557 (Nov. 2002).

Armand, R. et al., Treating Coagulopathy in Trauma Patients, Transfusion Medicine Reviews, vol. 17(3). pp. 223-231 (2003).

Arvieux, C. et al., Damage control laparotomy for haemorragic abdominal trauma, Annales De Chiruaie. vol. 128, pp. 150-158 (2003).

Becton, D. et al., Treatment of Bleeding with rFVIIa (NovoSeven®) in Four Diverse Cases, Blood, vol. 98(11), pp. 263a (2001).

Bianchi et al. Thromb Haemost., vol. 91(1), pp. 203-204 (2004).

Borgognone et al., Riv Ital Di Chi Plastica, Vol. 21(4), pp. 459-64 (1989).

Chiu, J. et al., Transfusion-sparing hemostatic agents, Transfusion Medicine, vol. 9, pp. 544-550 (2002).

Dejgaard, A., Update on Novo Nordisk's clinical trial programme on NovoSeven®, Blood Coagulation and Fibrinolysis. vol. 14(suppl), pp. 39-41 (2003).

Dutton, R. et al., Recombinant Factor VIIa for Controlling of Hemorrhage: Early Experience in Critically Ill Trauma Patients, Journal of Clinical Anesthesia, vol. 15, pp. 184-188 (2003).

Eikelboom, J. et al., Recombinant Activated Factor VIIa for Massive Hemorrhage in Non-Hemophiliac Patients: The Australian Experience, Blood, vol. 100(11), p. 2800 (2002).

Eikelboom, J.W. et al., Recombinant activated factor VII for the treatment of life-threatening haemorrhage, Blood Coagulation and Fibrinolysis, vol. 14, pp. 713-717 (2003).

Erhardtsen, E., Ongoing NovoSeven® Trials, Intensive Care Medicine, vol. 28, pp. 248-55 (2002).

Erhardtsen, E., To General Haemostasis-the Evidence-Based Route, Pathophysiology of Haemostasis and Thrombosis, vol. 32(suppll), pp. 47-52 (200).

Essex, D. et al., 42nd Annual Meeting of the American Society of Hematology, Dec. 1-5, 2000.

Essex, D. et al., Successful Use of Recombinant Factor VIIa for Trauma-Associated Massive Hemorrhage, Blood, vol. 96(11Pat), p. 268A (2000).

Grounds, Mike, Recombinant factor VIIa and its use in severe bleeding in surgery and trauma: a review, Blood Reviews, vol. 17, pp. S11-S21 (2003).

Hardy, J-F., Managing uncontrolled hemorrhage in trauma and surgery: a novel and promising approach, Canadian Journal of Anesthesia, vol. 49(suppl), pp. 84-86 (2002).

Hedner, U., General Haemostatic Agents- Fact or Fiction?, Pathophysiology of Haemostasis and Thrombosis, vol. 32(suppl 1), pp. 33-36 (2002).

Holcomb, J., Discussion, The Journal of Trauma, vol. 51(3), pp. 438-439 (2001).

Holcomb, J.B. et al., Use of Recombinant FAIIa for Intraperitoneal Coagulopathic Bleeding in a Septic Patient, Current Surgery, vol. 60(4), pp. 423-427 (2003).

Horton, J.W., Toxicology, vol. 189, pp. 75-88 (2003).

Jeroukhimov, I. et al., Early Injection of High-Dose Recombinant Factor VIIa Decreases Blood Loss and Prolongs Time from Injury to Death in Experimental Liver Injury, The Journal of Trauma, vol. 53(6), pp. 1053-1057 (2002).

Kampruisen, P.W. et al., Control of Life-Threatening Pulmonary Bleeding with Activated Recombinant Factor VII, The American Journal of Medicine, vol. 112, pp. 332-333 (2002).

Kenet, G. et al., Treatment of traumatic bleeding with recombinant factor VIIa, The Lancet, vol. 354, p. 1879 (1999).

Kristensen, A.T. et al., Potential uses of recombinant human factor VIIA in veterinary medicine, The Veterinary Clinics of North America Small Animal Practice, vol. 33, pp. 1437-1451 (2003).

Kulkarni, R. et al., Recombinant factor VIIa use in paediatric traumatic liver injuries in children, JVF Congress of WHF Seville, abstract, (2002).

Lynn, M. et al., Early Use of Recombinant Factor VIIa Improves Mean Arterial Pressure and May Potentially Decrease Mortality in Experimental Hemorrhagic Shock: A Pilot Study, The Journal of Trauma, vol. 52, pp. 703-707 (2002).

Lynn, M. et al., Updates in the management of severe coagulopathy in trauma patients, Intensive Care Medicine, vol. 28, pp. 241-247 (2002).

Martinowitz, U. et al., Meeting Abstract, 43rd Annual Meeting of the American Society of Hematology, Part 1, Dec. 7-11, 2001.

Martinowitz, U. et al., Intravenous rFVIIa Administered for Hemorrhage Control in Hypothermic Coagulopathic Swine with Grade V Liver Injuries, The Journal of Trauma, vol. 50, pp. 721-729 (2001).

Martinowitz, U. et al., New Approach for the Management of Catastrophic Bleeds in Trauma and Surgery: Enhancement of Coagulation at the Site of Injury by Recombinant Activated Factor VII, Blood, vol. 98, pp. 827A-828A (2001).

Martinowitz, U. et al., Possible role of recombinant activated factor VII in the control of hemorrhage associated with massive trauma, Canadian Journal of Anesthesia, vol. 49(suppl. 2), pp. 15-20 (2002).

Martinowitz, U. et al., Recombinant Activated Factor VII for Adjunctive Hemorrhage Control in Trauma and Surgey: the Isreali Compassinate Registry, Thrombosis and Haemostasis, suppl.,(2001).

Martinowitz, U. et al., Recombinant Activated Factor VII for Adjunctive Hemorrhage Control in Trauma, The Journal of Trauma, vol. 51(3), pp. 431-439 (2001).

Meng, Z.H. et al., The Effect of temperature and pH on the Activity of Factor VIIa: Implications for the Efficacy of High-Dose Factor VIIa in Hypothermic and Acidotic Patients, The Journal of Trauma, vol. 55, pp. 886-891 (2003).

Morenski, J.D. et al., Recombinant activated VII for cerebral injury-induced coagulopathy in Pediatric patients. Journal of Neurosuraerv, vol. 98, pp. 611-616 (2003).

Murkin, J.M. et al., A novel hemostatic agent: the potential role of recombinant activated factor VII (rFVIIa) in anesthetic practice, Canandian Journal of Anesthesia, vol. 49(10)(suppl.), pp. S21-S26 (2002).

O'Neill, P.A. et al., Successful Use of recombinant Activated Factor VII for Trauma-Associated Hemorrhage in a Patient without Preexisting Coagulopathy, The Journal of Trauma, vol. 52(2), pp. 400-405 (2002).

Park, P. et al., Recombinant Activated Factor VII for the Rapid Correction of Coagulopathy in Nonhemophilic Neurosurgical Patients, Neurosurgery, vol. 53(1), pp. 34-39 (2003).

Robbins, D. et al., Successful treatment of High Titer Inhibitors in Mild Hemophilia A with Avoidance of Factor VIII and Immunosuppressive Therapy, American Journal of Hematology, vol. 68, pp. 184-188 (2001).

Sapsford, W., Trauma, vol. 4(2), pp. 117-123 (2002).

Schreiber, M.A. et al., The Effect of Recombinant Factor VIIa on Coagulopathic Pigs with Grade V Liver Injuries, The Journal of Trauma, vol. 53(2), pp. 252-259 (2002).

Schuster, R. et al., Treatment of Bleeding in Severe Hemorrhagic Pancreatitis with recombinant Factor VIIa. The American Surgeon. vol. 69 (11), pp. 1017-1018 (2003).

Siegel, L.J. et al., Cerebral Sinus Thrombosis in a Trauma Patient after Recombinant Activated Factor VII Infusion, Anesthesiology, vol. 11(2), pp. 441-443 (2004).

Susmann, G. et al., Early intensive care unit intervention for trauma care: what alters the outcome?, Current Opinion in Critical Care, vol. 8(6), pp. 587-592 (2002).

Dincer et al., "Human Recombinant Activated Factor Seven, Novoseven (rVIIa), in the Management of Massive Bleeding Despite Adequate Resuscitation in Major Trauma," Disorders of Coagulation or Fibrinolysis, Blood. 2002;100(11), Abstract #3918, p. 110b.

U.S. Appl. No. 11/579,680, filed Nov. 7, 2006, Johannson et al.

Sato et al., "Tissue factor pathway inhibitor inhibits aortic smooth muscle cell migration induced by tissue factor/factor VIIa complex," Thrombosis Haemostasis, vol. 97, pp. 1138-1141 (1997).

Taniguchi et al., "Enhanced Expression of Urokinase Receptor Induced through the Tissue Factor VIIa Pathway in Huma Pancreatic Cancer", (1998) Cancer Res., vol. 58, pp. 4461-4467.

Pendurthi et al., "Binding of Factor VIIa to Tissue Factor Induces Alterations in Gene Expression in Human Fibroblast Cells: Up-regulation of Poly(A) Polymerase," (1997) Proc. Natl. Acad. Sci., vol. 94, pp. 12598-12603.

Camerer et al., "Coagulation Factors VIIa and Xa Induce Cell Signaling Leading to Up-regulation of the egr-1 Gene," (1999) J Biol. Chem., vol. 274, No. 45, pp. 32225-32233.

Pendurthi et al., "Factor VIIa and Thrombin Induce the Expression of Cyr61 and Connective Tissue Growth Factor," (2000) J. Biol. Chem., vol. 275, No. 19, pp. 14632-14641.

Ollivier, J.C. et al., "Vascular Endothelial Growth Factor Production by Fibroblasts in Response to Factor VIIa Binding to Tissue Factor Involves Thrombin and Factor Xa," Arteriosclerosis, Thrombosis, and Vascular Biology, 2000, vol. 20, pp. 1374-1381.

Ollivier et al., "Tissue Factor-Dependent Vascular Endothelial Growth Factor Production by Human Fibroblasts in Response to Activated Factor VII," (1998) Blood, vol. 91, No. 8, pp. 2698-2703.

Niemi et al., "Haemostatic Disturbances in Burned Patients During Early Excision and Skin Grafting," (1998) Blood Coag. Fibrinol., vol. 9, pp. 19-28.

Cunningham et al., "Tissue Factor and Factor VIIa Receptor/Ligand Interactions Induce Proinflammatory Effects in Macrophages," (1999) Blood, vol. 94, No. 10, pp. 3413-3420.

Borgognone et al., "The Role of Antithrombin III and Factor VII in the Prognosis and Treatment of Burn Injury," (1969) The Italian Journal of Plastic Surgery, vol. 21, pp. 459-464.

Ingerslev J. et al., "Home Treatment with Recombinant Activated Factor VII: Results from One Centre," (1998) Blood Coagulation or Fibrinolysis, vol. 9 (Suppl 1), pp. S107-S110.

Petrini P. et al., "Treatment of Acute Bleeds with Recombinant Activated Factor VII During Immune Tolerance Therapy," (1998) Blood Coagulation or Fibrinolysis, vol. 9 (Suppl 1), pp. S143-S146.

Mueller et. al.; Journal of Clinical Investigation; 1998; vol. 101; pp. 1372-1378.

USE OF FACTOR VIIA OR A TISSUE FACTOR ANTAGONIST FOR REGULATING GENE EXPRESSION AND CELL MIGRATION OR CHEMOTAXIS

CROSS REFERENCE TO RELATED APPLICATIONS

This application is a continuation of 11/152,468, filed Jun. 14, 2005, now abandoned, which is a continuation of 10/051,044, filed Jan. 14, 2002, now abandoned, which is a continuation of PCT/DK00/00401 filed on Jul. 14, 2000, and claims priority under 35 U.S.C. 119 of Danish application no. PA 1999 01117 filed on Aug. 12, 1999, Danish application no. PA 1999 01023 filed on Jul. 14, 1999, and U.S. provisional application No. 60/148,300 filed on Aug. 11, 1999, the contents of which are fully incorporated herein by reference.

FIELD OF INVENTION

A novel cell regulating activity of coagulation factor VII (FVII) or a tissue factor antagonist such as, for example, inactivated coagulation factor VIIa (FVIIai) of cells expressing tissue factor (TF) has been described. The present invention relates to a method for regulating cell migration or chemotaxis by contacting the cell with FVIIa or another TF agonist, or FVIIai or another TF antagonist and determining the migration of said cell. The invention also relates to the use of FVIIa or another TF agonist, or FVIIai or another TF antagonist for the preparation of a medicament for regulation of cell migration in a patient. Moreover the present invention relates to a method of treatment, and a method of detecting the activity of compounds, in particular drug candidates that interact with cell migration.

BACKGROUND OF THE INVENTION

The extrinsic pathway of blood coagulation is initiated when FVIIa circulating in plasma binds to the integral-membrane protein, tissue factor (TF). The role of TF in blood coagulation has been extensively studied. The involvement of FVIIa as a proteolytic enzyme in the blood coagulation cascade is believed to be confined to the extracellular leaflet of TF expressing cells. An intracellular activity of FVIIa was first implied when the sequence of TF showed homology to the cytokine/interferon- or heamatopoietic receptor superfamily. The subclass I of the heamotopoietic receptor family includes receptors for growth hormone, prolactin, interleukins 1 to 7, granulocyte-macrophage colony stimulating factors, erythropoitin and thrombopoitin. Subclass II includes TF and receptors for interferon a and b.

The resemblance of TF to this class of receptors was further substantiated with the appearance of the crystal structure. Characteristic of this class of cytokine receptors that includes receptors for interferon b and g and IL-10 is that their activation lead to rapid tyrosine phosphorylation of the receptors themselves, as well as a subset of intracellular proteins. Within minutes after the initial tyrosine phosphorylation an array of mitogen-activated (Ser/Thr) kinases (MAPK) is activated. These kinases are arranged in several parallel signalling pathways. Thorough studies of the putative intracellular signalling capacity of FVIIa have shown that it induce mobilisation of intracellular free calcium ($Ca^{2+}$) in the human bladder carcinoma cell line, J82, which constitutively express TF and in umbelical vein endothelial cells which were pretreated with interleukin-1 to express TF, but have failed to show any cytokine-like activation of intracellular tyrosine kinases. In conclusion FVIIa is believed, in a TF dependent manner, to induce mobilisation of intracellular $Ca^{2+}$ through activation of phospholipase C. The mechanism by which FVIIa activates phospholipase c is not known, but tyrosine kinase activation has specifically been ruled out.

Recent reports from a number of laboratories indicate that TF may influence an array of important biological functions other than coagulation., such as angiogenesis, embryo vascularization and tumor metastasis. At present, however, it is unclear how TF contributes to these biological processes. The extracellular domain of TF consists of two fibronectin-type III-like modules, as in the typical class II cytokine receptor extracellular domain, raising the possibility that TF may play a role in signal transduction, the primary function of cytokine receptor. However, TF has a very short cytoplasmic domain (only 21 amino acid residues in length) and lacks membrane-proximal motifs that mediate binding of the non-receptor Janus kinases (Jaks) that are essential for cytokine receptor signaling. Nonetheless, several biochemical findings suggest a signal transduction function for TF. Analysis of the human TF protein sequence revealed a putative phosphorylation site in the cytoplasmic domain, which is conserved in mouse, rat and rabbit TF. Specific serine residues in the cytoplasmic tail of TF are phosphorylated in cells following stimulation with protein kinase C activator. The human TF cytoplasmic tail is phosphorylated in vitro at multiple sites when incubated with lysates of U87-MG cells. A potential role for the TF cytoplasmic domain in signal transduction is also indicated in studies that showed prometastatic function of TF is critically dependent on the TF cytoplasmic domain. Further, TF cytoplasmic domain is shown to interact with actin-binding protein 280 (ABP-280) and supports cell adhesion and migration through recruitment of ABP-280 to TF-mediated adhesion contacts.

However, TF has also been shown to participate certain types of cell signaling by serving as a cofactor for its physiological ligand FVIIa in an extracellular signaling by a proteolytic mechanism. For example, binding of FVIIa to cell surface TF is shown to induce intracellular $Ca^{2+}$ oscillations in a number of TF expressing cells, transient phosphorylation of tyrosine in monocytes, activation of MAP kinase, alteration in gene expression in fibroblasts and enhanced expression of urokinase receptor in tumor cells. Catalytically inactive FVIIa (FVIIai) fails to induce many of the above signaling responses, from $Ca^{2+}$ oscillations to MAP kinase activation and gene reduction, and it appears that the catalytic activity of FVIIa may be required for at least some TF-FVIIa-mediated signal transduction. At present, not much is known about signaling pathway(s) that are induced by proteolytically active FVIIa and how the signals generated by FVIIa could contribute to angiogenesis and tumor metastasis.

To study temporal program of transcription that underlies the FVIIa-induced response, in the present study, we have examined the response of human fibroblasts to FVIIa using a cDNA microarray. The data revealed that the cellular expression of several genes was detectably altered in fibroblasts upon exposure of to FVIIa. One such gene is Cyr61, a growth factor-inducible intermediate early gene, whose product is shown to promote cell adhesion, augment growth factor-induced DNA synthesis and stimulate cell migration in fibroblasts and endothelial cells.

SUMMARY OF THE INVENTION

The present invention relates to usage of FVII and/or FVIIa and/or another TF agonist and/or FVIIai and/or another TF antagonist in therapeutic treatment of pathological conditions that can be related to cell migration or treated by specific regulation of cell migration or chemotaxis.

In another aspect the invention relates to the use of FVII and/or FVII and/or another TF agonist and/or FVIIai and/or another TF antagonist in therapeutic treatment of pathological conditions that can be related to the regulation of expression of at least one gene in a cell e.g. the Cyr61 gene.

In another aspect the invention relates to a method for inducing or enhancing cell migration, comprising the step of contacting said cell with a tissue factor agonist In one embodiment, the tissue factor agonist is FVII or FVIIa.

In another aspect the invention relates to a method of reducing or inhibiting cell migration, comprising the step of contacting the cell with a tissue factor antagonist.

In one embodiment the tissue factor antagonist is modified FVII.

In one embodiment the cell is a human cell expressing tissue factor, including fibroblasts, smooth muscle cells, tumour cells, haematopoietic cells and epithelial cells.

In one embodiment the modified factor VII is selected from factor VII modified with Dansyl-Phe-Pro-Arg chloromethyl ketone, Dansyl-Glu-Gly-Arg chloromethyl ketone, Dansyl-Phe-Phe-Arg chloromethyl ketone, Phe-Phe-Arg chloromethylketone, Dansyl-D-Phe-Pro-Arg chloromethyl ketone, Dansyl-D-Glu-Gly-Arg chloromethyl ketone, Dansyl-D-Phe-Phe-Arg chloromethyl ketone and D-Phe-Phe-Arg chloromethylketone.

In another aspect the invention relates to a method for inducing or enhancing wound healing in a patient, comprising administering to said patient an effective amount of a pharmaceutical composition comprising Factor VIIa or factor VII or another tissue factor agonist or a combination thereof.

In another aspect the invention relates to a method for inhibiting or reducing cell migration, invasion, migration-induced cell proliferation or angiogenesis in a patient having a disease or condition associated with undesired cell migration, invasion, migration-induced cell proliferation or angiogenesis, comprising administering to said patient an effective amount of a pharmaceutical composition comprising a tissue factor antagonist.

In one embodiment the disease or condition is primary tumour growth, tumour invasion or metastasis.

In another aspect the invention relates to the use of a tissue factor agonist for the manufacture of a medicament for inducing or enhancing cell migration.

In another aspect the invention relates to the use of a tissue factor antagonist for the manufacture of a medicament for reducing or inhibiting cell migration.

In another aspect the invention relates to a method of regulating the expression of at least one gene in a cell, comprising the step of either contacting said cell with a tissue factor agonist or contacting said cell with a tissue factor antagonist.

In one embodiment the gene is a gene belonging to the CCN gene family.

In another embodiment the gene is selected from the group consisting of Cyr61, CTFG, dopamine D2 receptor, EST Incyte PD 395116 or P2U nucleotide receptor.

In one embodiment the gene is Cyr61 gene.

In one embodiment the regulation is inducing or enhancing expression. In another embodiment the regulation is reducing or inhibiting expression.

In one embodiment FVII or FVIIa or another tissue factor agonist induces or enhances gene expression and modified FVII or another tissue factor antagonist reduces or inhibits gene expression, e.g. when the gene is a gene belonging to the CCN gene family, or the gene is selected from the group consisting of Cyr61, CTFG, dopamine D2 receptor, EST Incyte PD 395116 or P2U nucleotide receptor.

In another embodiment FVII or FVIIa or another tissue factor agonist reduces or inhibits gene expression, and modified FVII or another tissue factor antagonist induces or enhances gene expression, e.g., when the gene is EST PD674714.

Diseased states, which may be treated, are pathological conditions such as, for example, atherosclerosis, tumour deposition, tumour growth, tumour invasion, metastasis, or angiogenesis. Other states that may be treated is, for example, healing of wounds including regeneration of vessel walls and treatment of burns, or inflammation, or the regulation of cell migration in vitro such as, for example, growing of tissue.

LIST OF FIGURES (fra 6011)

Figure 1B:
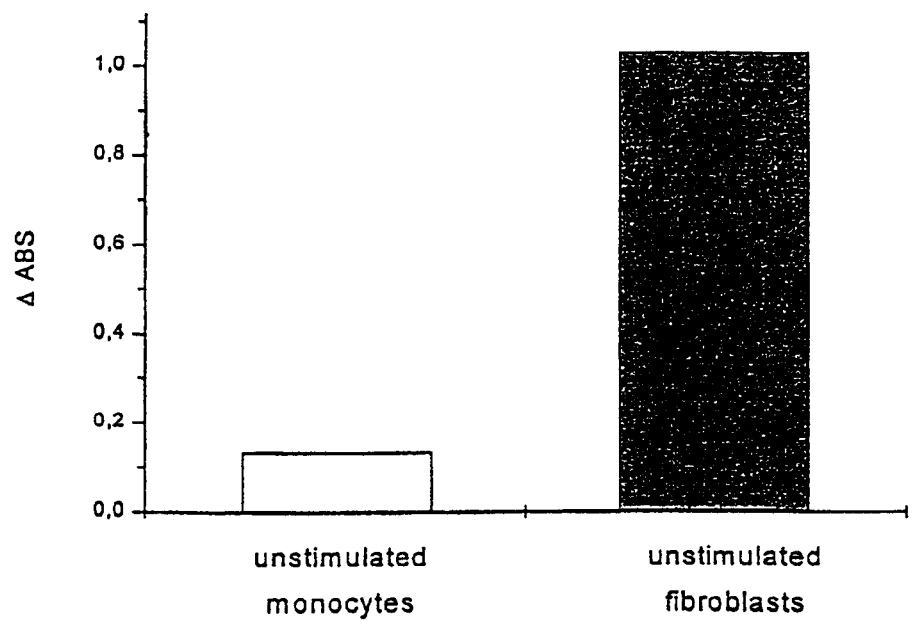

FIGS. 1A and 1B: Flow cytometric analysis of TF expression in fibroblasts (1A). The cells were stained with either a murine monoclonal fluoresceinisothiocyanate (FITC)-conjugated mouse anti IgG-antibody (unfilled area) that was used as negative control or a monoclonal FITC-conjugated anti-tissue factor (TF) antibody (filled area). FIG. 1B shows the procoagulant activity of fibroblasts. Fibroblasts with TF expression generated a 10-fold increase in PCA compared to monocytes without TF expression.

Figure 2:
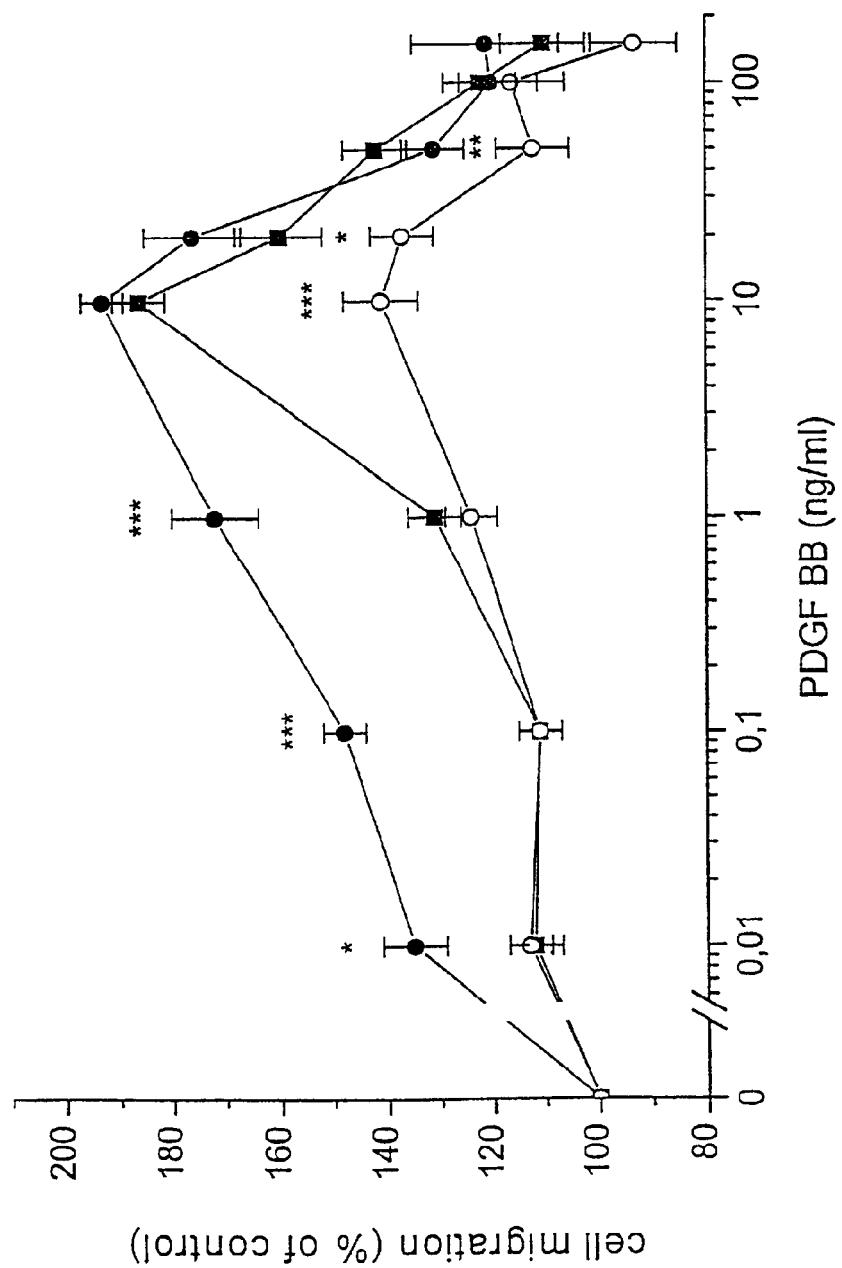
Figure 3A:
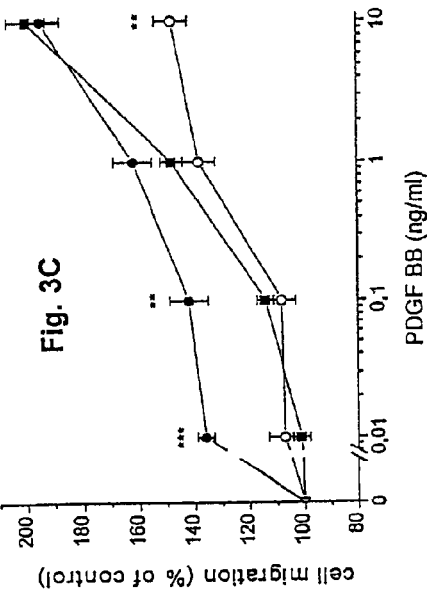
Figure 3C:
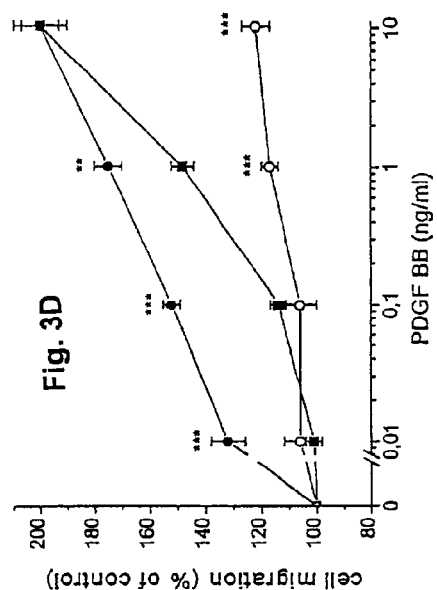
Figure 3B:
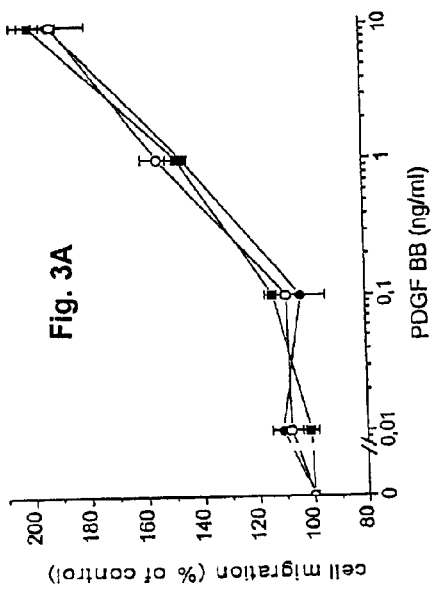
Figure 3D:
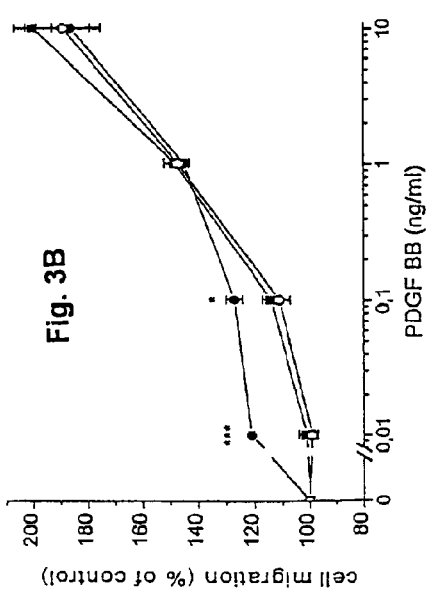

FIG. 2: Effects of FVIIa and FFR-FVIIa on PDGF-BB induced chemotaxis in human fibroblasts. .nu. show the chemotactic response of fibroblasts to different concentrations of PDGF-BB. Fibroblasts incubated with 100 nM FVIIa ($\lambda$) or 100 nM FFR-FVIIa ($\mu$) migrated towards different concentrations of PDGF-BB. Results are means and SEM of three separate experiments. P-values less than 0.05, * was considered statistically significant (Student's t test).

FIG. 3A-D: The influence of different concentrations of FVIIa or FFR-FVIIa on PDGF-BB induced chemotaxis in fibroblasts. v show migration of fibroblasts to different concentrations of PDGF-BB. Cells were incubated with 12.5 (A), 25 (B), 50(C) and 100 (D) nM FVIIa ($\lambda$) or FFR-FVIIa ($\mu$) and assayed in the Boyden chamber towards different concentrations of PDGF-BB. Results are mean and SEM of three different experiments. *=$p<0.05$, =$p<0.01$ and *=$p<0.001$ Student's t test.

Figure 4:
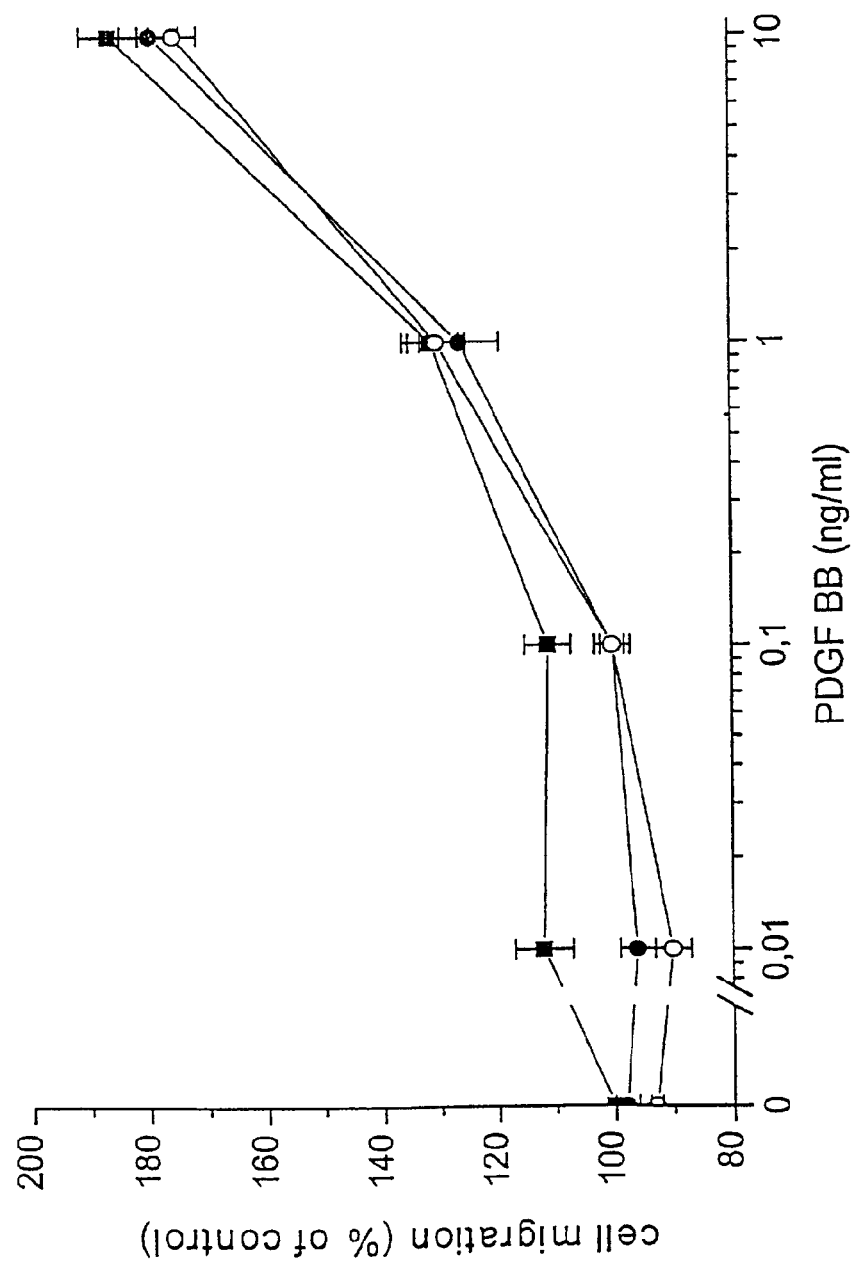

FIG. 4: A mixture of three monoclonal antibodies to TF blocks the effects of FVIIa and FFR-FVIIa on PDGF-BB induced chemotaxis in fibroblasts. v show migration towards PDGF-BB of fibroblasts without TF antibodies, $\lambda$ fibroblasts preincubated with TF antibodies and 100 nM FVIIa, and .mu. fibroblasts preincubated with TF antibodies and 100 nM FFR-FVIIa. Results are mean and SEM of three separate experiments.

Figure 5A:
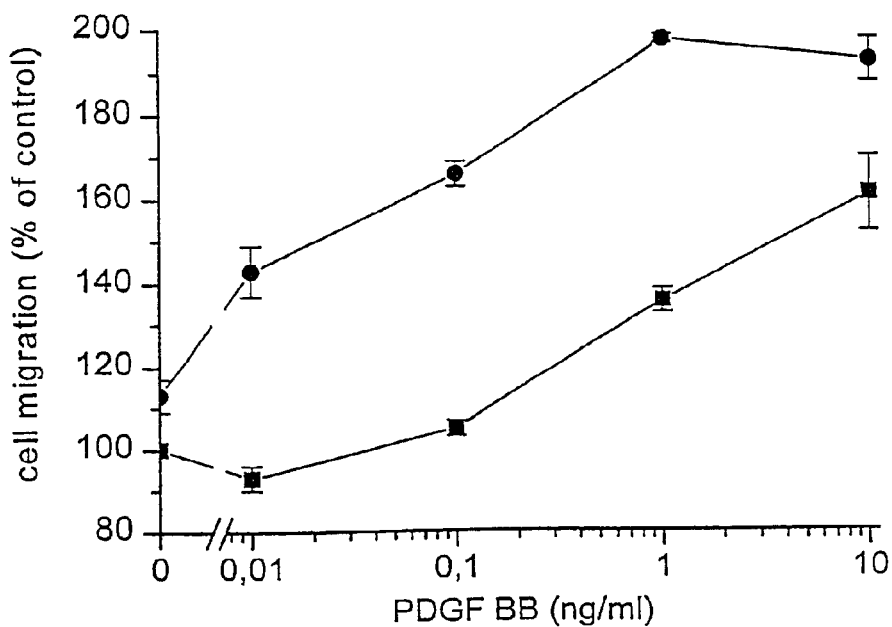
Figure 5B:
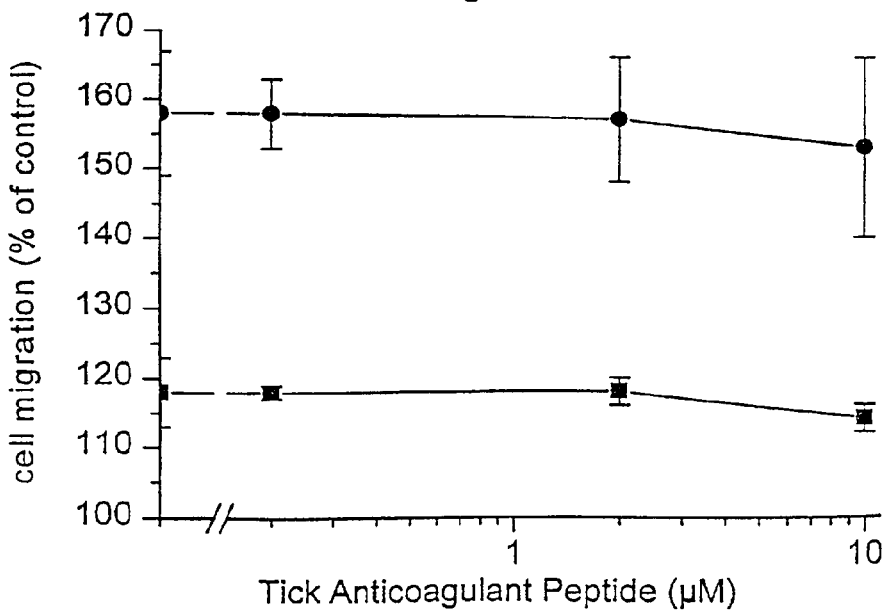

FIGS. 5A and 5B: The influence of FXa on the chemotactic response to PDGF-BB induced by FVIIa. Fibroblasts were preincubated with 200 nM TAP (FIG. 5A) (v) or with 0.2-2 $\mu$M TAP (FIG. 5B) (v) and then with 100 nM FVIIa ($\lambda$). TAP was present during the entire experiments. Chemotaxis was induced by different concentrations of PDGF-BB (5A) or by 0.1 ng/ml PDGF-BB (5B). Results are mean and SD of two separate experiments.

Figure 6:
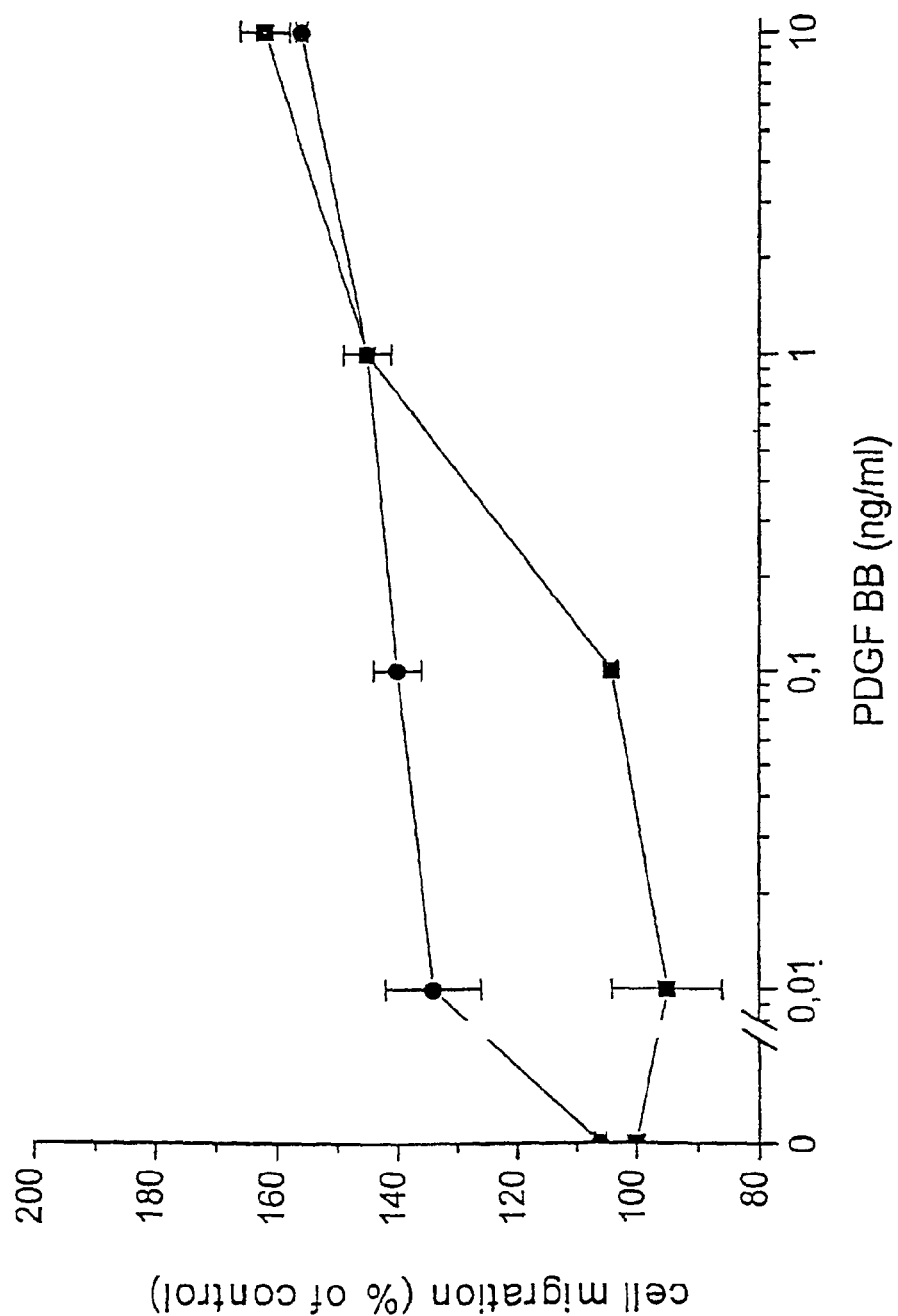

FIG. 6: The influence of thrombin on the chemotactic response to PDGF-BB induced by FVIIa. Fibroblasts were preincubated with 5 U/mL (final concentration) Hirudin and then with 100 nM FVIIa. Hirudin was present during the entire experiments. Chemotaxis was induced by different concentrations of PDGF-BB. v show cells incubated with Hirudin alone and $\lambda$ cells with Hirudin and FVIIa. Results are mean and SD of two separate experiments.

Figure 7:
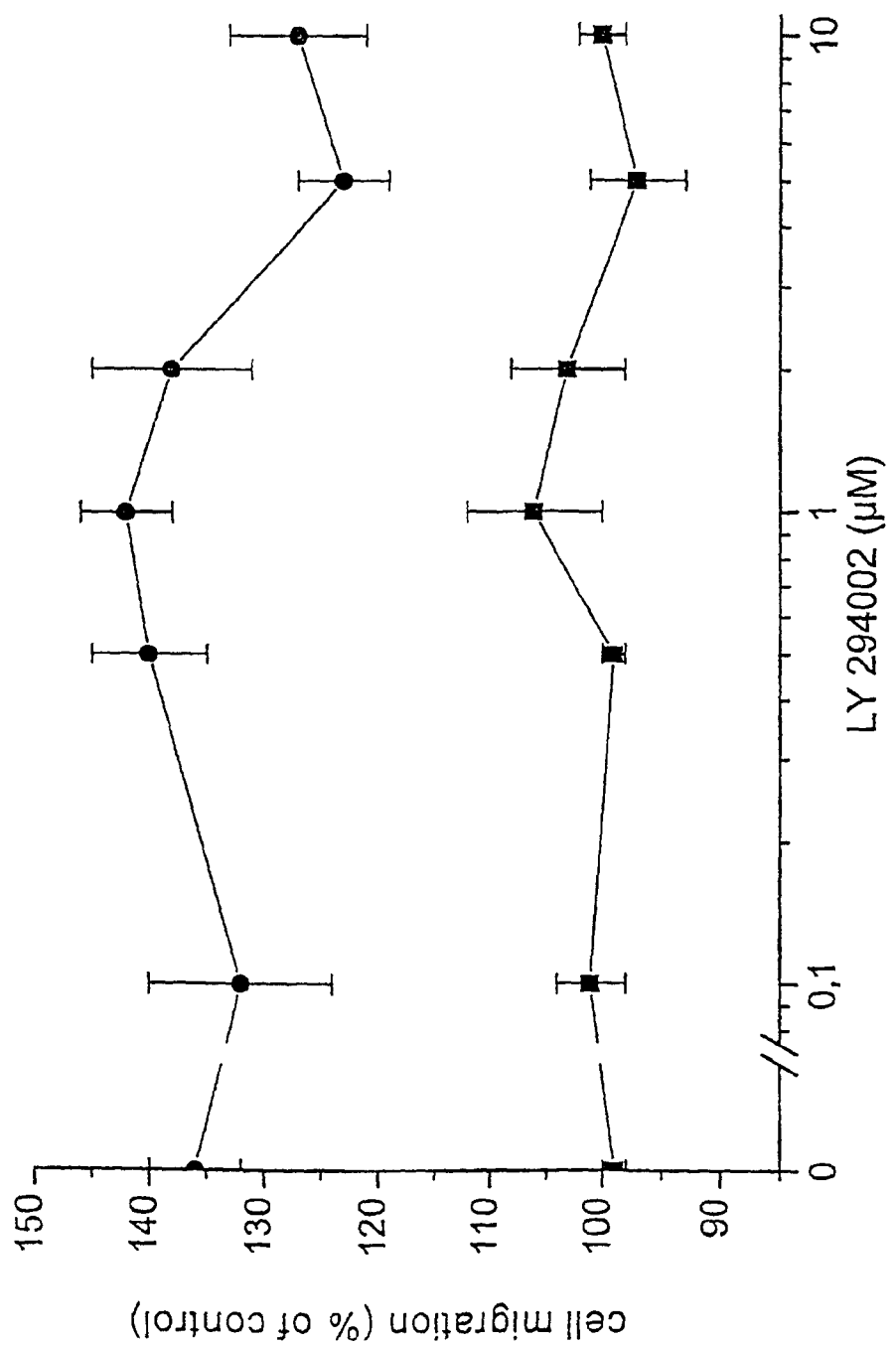

FIG. 7: Effect of inhibition of PI3'-kinase on chemotaxis in fibroblasts incubated with FVIIa. Cells were preincubated with varying concentrations of LY294002 for 30 min at 37° C., and then with 100 nM FVIIa (λ) or without FVIIa (v). The inhibitor was present throughout the chemotaxis assay. Chemotaxis was induced by 0.1 ng/mL PDGF-BB. Results are mean and SD of two separate experiments.

Figure 8A:
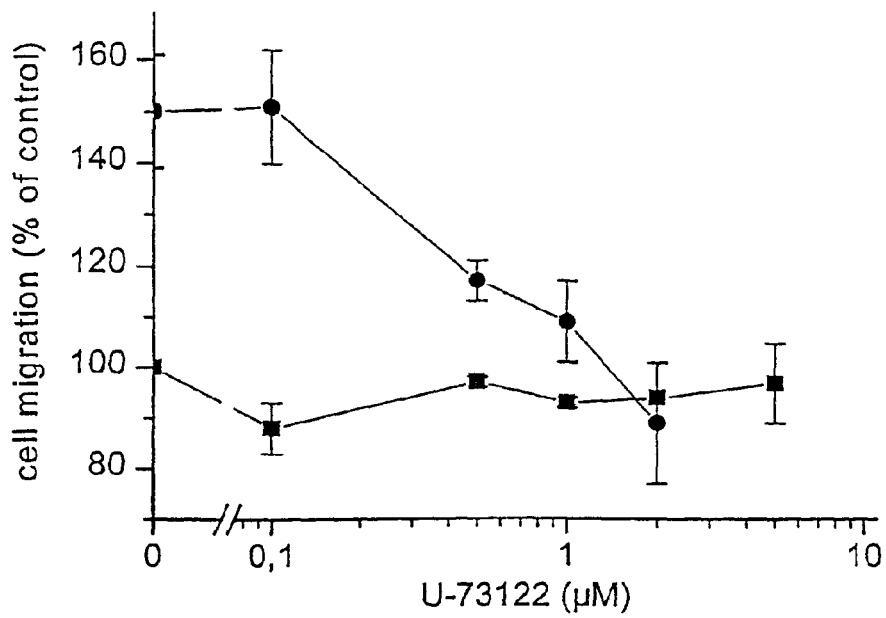
Figure 8B:
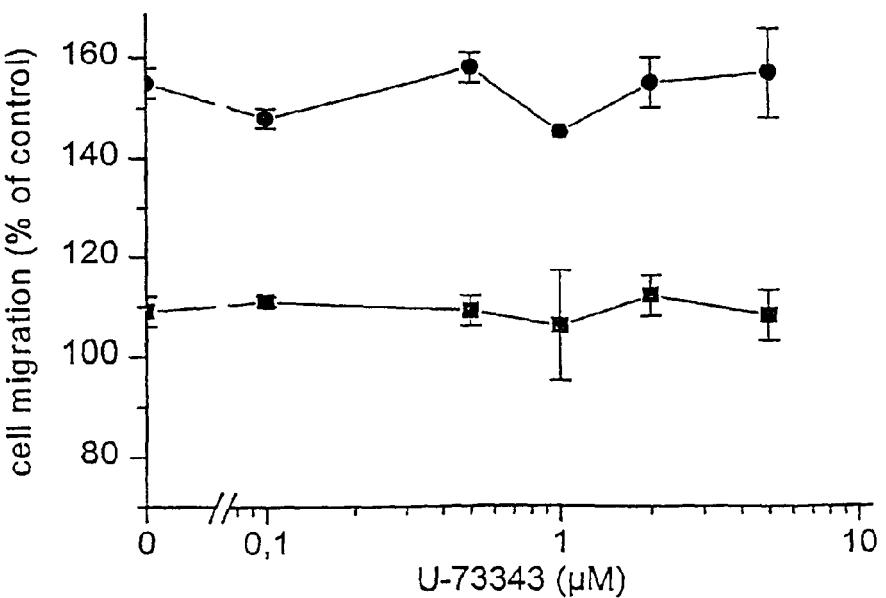

FIGS. 8A AND 8B: Effect of inhibition of PLC on chemotaxis in fibroblasts incubated with FVIIa. Cells were incubated with varying concentrations of U73122 (active PLC inhibitor) (8A) or U73343 (inactive control) (8B) for 30 min at 37° C. before incubation with or without 100 nM FVIIa, and then assayed in the Boyden chamber to a concentration gradient of 0.1 ng/mL PDGF-BB. The agents were present during the entire experiments. v show cells with U73122 or U73343 alone, λ cells with U73122 or U73343 and FVIIa. Results are mean and SD of two separate experiments.

Figure 9:
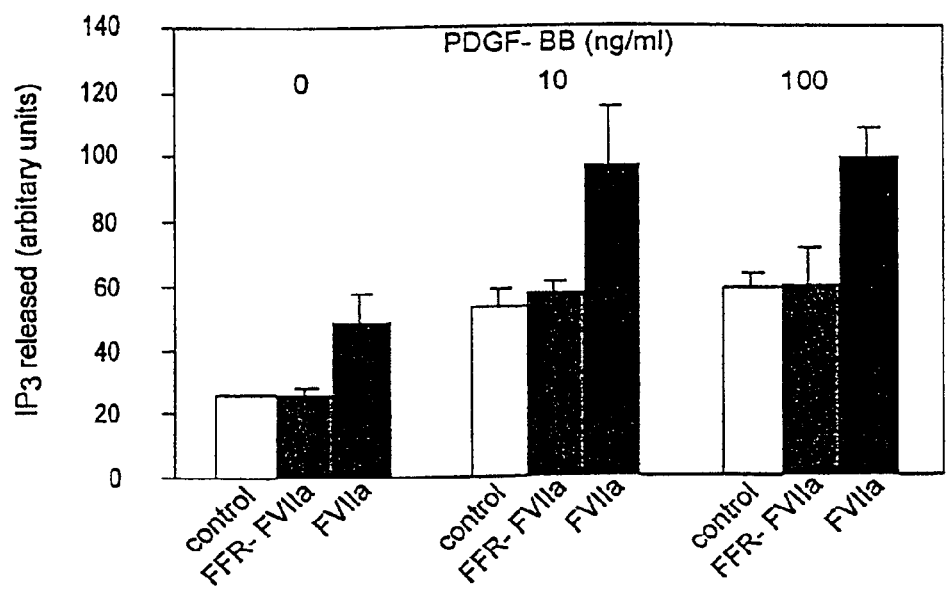

FIG. 9: Release of inositol trisphosphate ($IP_3$) from fibroblasts stimulated with FVIIa, FFR-FVIIa alone or in combination with PDGF-BB. Cells were labelled over night with myo [$^3$H] inositol, incubated with or without 100 nM FVIIa or FFR-FVIIa in the absence or presence of 10 ng/mL or 100 ng/mL PDGF-BB. Cells were then analysed for release in $IP_3$. Open bars show cells without FVIIa or FFR-FVIIa (control), hatched bars show cells with FFR-FVIIa, and black bars show cells incubated with FVIIa.

Figure 10:
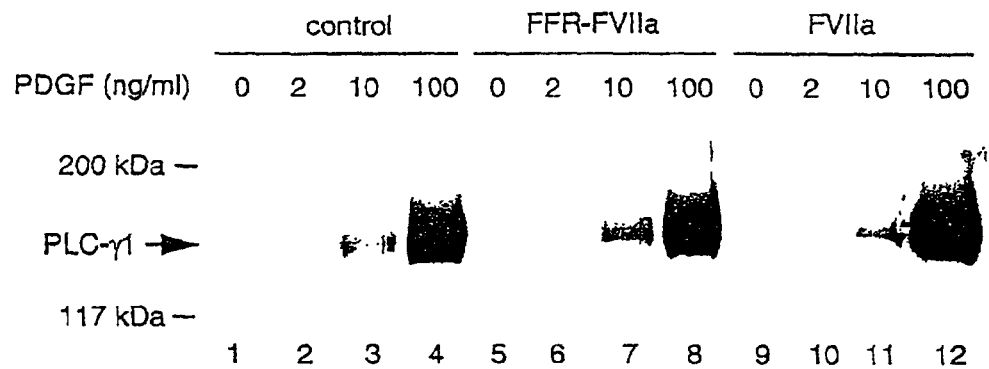

FIG. 10: Tyrosine phosphorylation of PLC-γ1 in response to PDGF-BB alone (control), FVIIa or FFR-FVIIa in combination with PDGF-BB. Cells were incubated with 100 nM FVIIa or FFR-FVIIa for one hour, and then with or without PDGF-BB at indicated concentrations. Cells were lysed and tyrosine phosphorylation of PLC-γ1 detected as described in methods.

Figure 11:
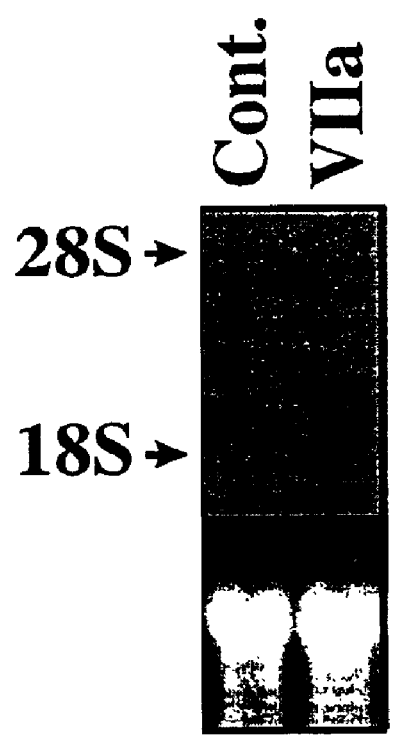

FIG. 11. Northern blot analysis confirming the data obtained with cDNA microarray assay. Ten μg of total RNA (from the same RNA samples that were used to isolate poly (A) RNA to generate probes for hybridization of cDNA microarray) were patiented to Northern blot analysis and probed with $^{32}$P-labeled Cyr61 (a partial length cDNA, obtained from Genomic Systems). Panel B. The hybridization signals are quantified with PhosphorImager (Molecular Dynamics).

Figure 12:
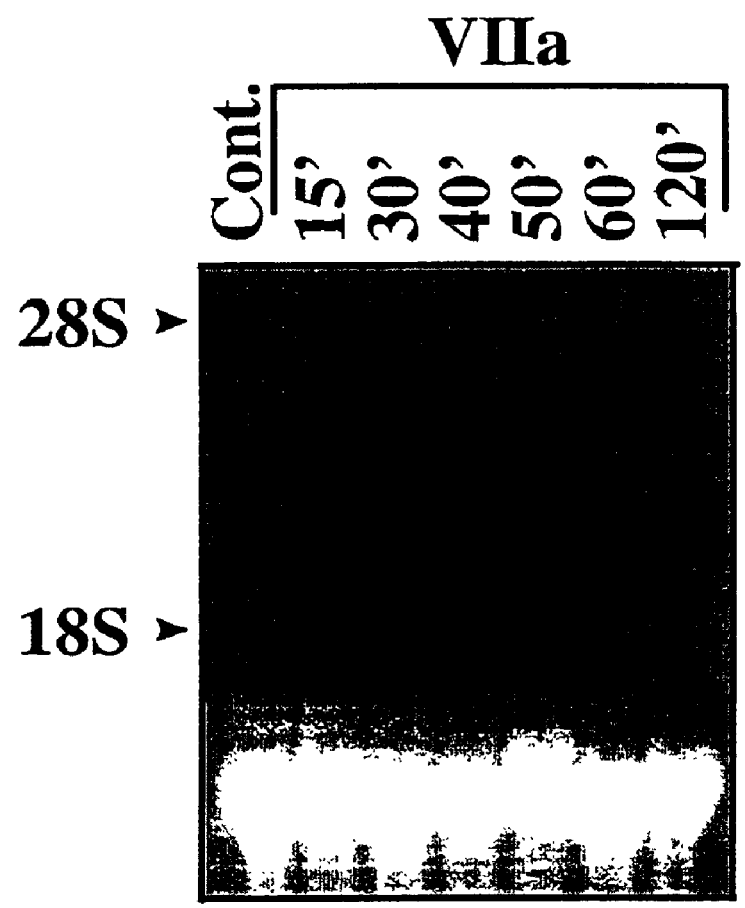

FIG. 12. Time-dependent factor VIIa-induced expression of Cyr61. Quiescent monolayers of WI-38 cells were treated with factor VIIa (5 μg/ml) for varying time periods. Total RNA (10 μg) was patiented to Northern blot analysis and probed with radio labeled Cyr61. Ethidium bromide staining of 28S ribosomal RNA of the corresponding blot is shown in the bottom panel as RNA loading control.

Figure 13:
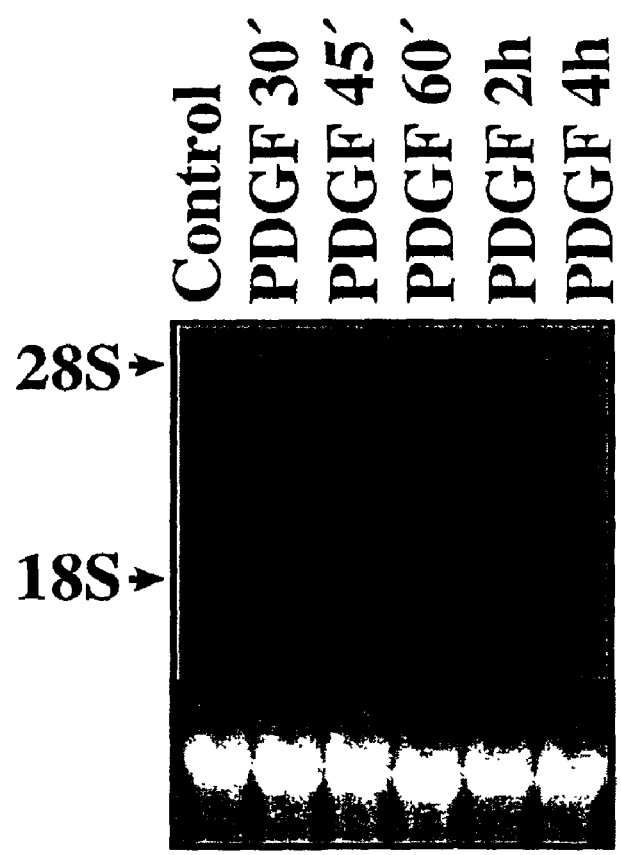

FIG. 13. Time-dependent factor Vila-induced expression of Cyr61. Quiescent monolayers of WI-38 cells were treated with PDGF-BB (10 ng/ml) for varying time periods. Total RNA (10 μg) was patiented to Northern blot analysis and probed with radio labeled Cyr61. Ethidium bromide staining of 28S ribosomal RNA of the corresponding blot is shown in the bottom panel as RNA loading control.

Figure 14:
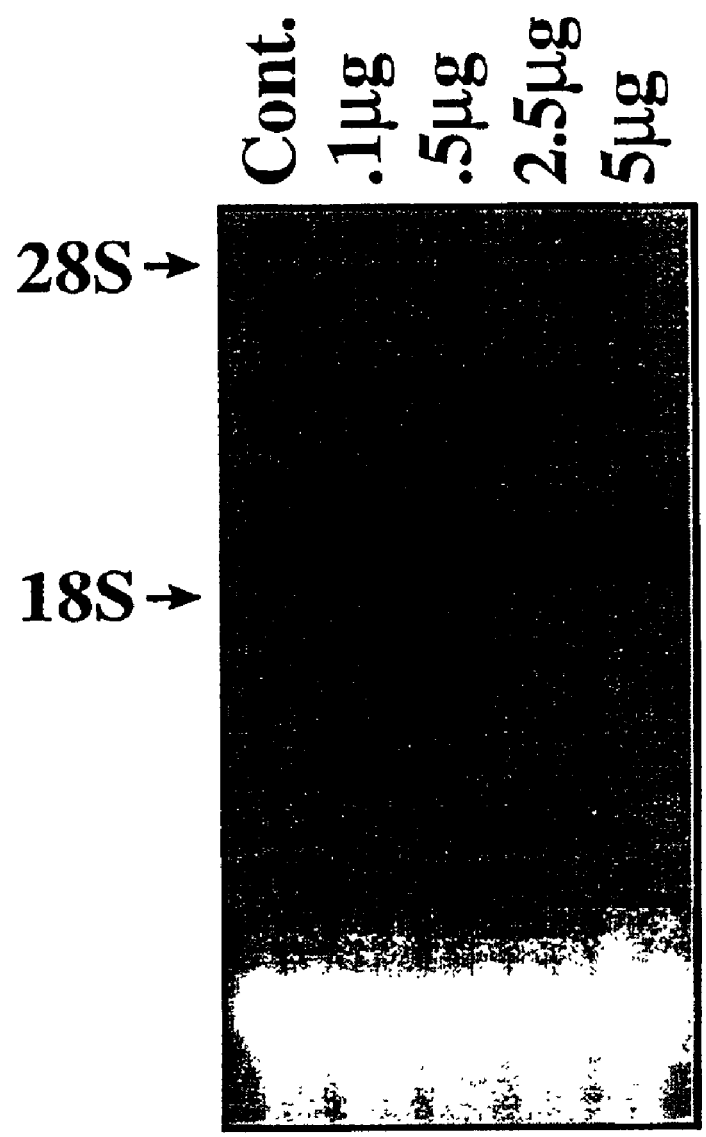

FIG. 14. Dose-dependent factor VIIa-induced expression of Cyr61. Quiescent monolayers of WI-38 cells were treated with varying doses of factor VIIa, 0, 0.1, 0.5, 2.0 and 5.0 μg/ml for 45 min. Total RNA (10 μg) was patiented to Northern blot analysis and probed with radiolabeled Cyr61. Ethidium bromide staining of 28S ribosomal RNA of the corresponding blot is shown in the bottom panel as RNA loading control.

Figure 15:
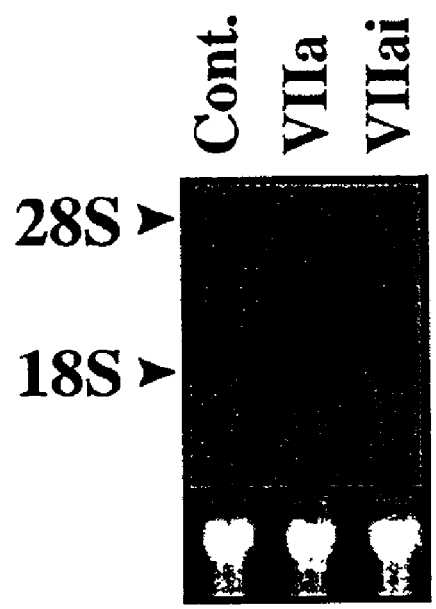

FIG. 15. Factor VIIa catalytic activity is required for the induced expression of Cyr61. Quiescent monolayers of WI-38 cells were treated with a control serum-free medium or serum-free medium containing factor VIIa (5 μg/ml) or active-site inactivated factor VIIa (VIIai, 5 μg/ml) for 45 min. Total RNA (10 μg) was patiented to Northern blot analysis and probed with radiolabeled Cyr61. Ethidium bromide staining of 28S ribosomal RNA of the corresponding blot is shown in the bottom panel as RNA loading control.

Figure 16:
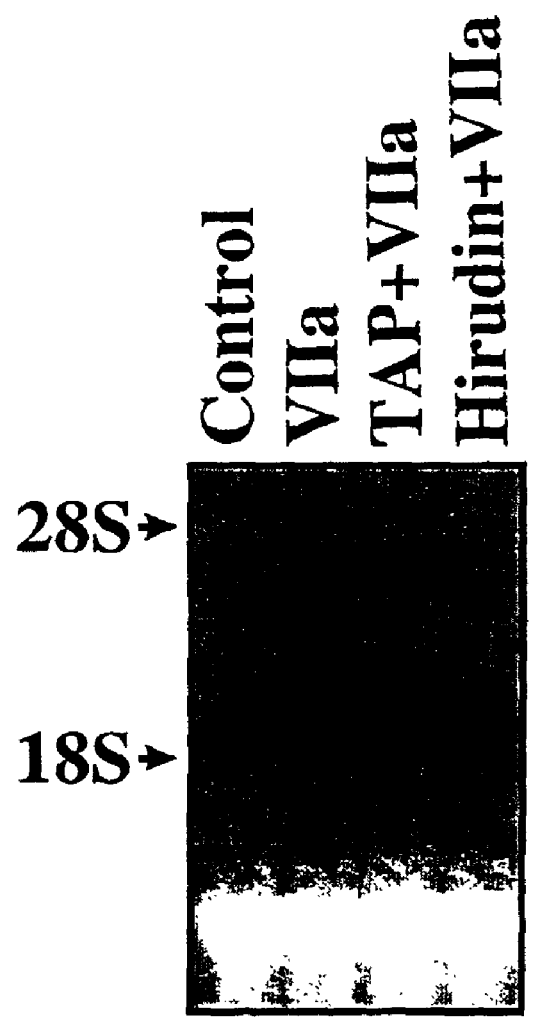

FIG. 16. Factor VIIa-induced expression of Cyr61 is not abolished by specific inhibitors of factor Xa and thrombin. Quiescent monolayers of WI-38 cells were treated with control medium or the medium containing factor VIIa (5 μg/ml; 100 nM for 45 min. Cells were preincubated with 200 nM recombinant TAP lane 3) or hirudin (lane 4) for 30 min before exposure to factor VIIa for 45 min. Total RNA (10 μg) was patiented to Northern blot analysis and probed with radiolabeled Cyr61. Ethidium bromide staining of 28S ribosomal RNA of the corresponding blot is shown in the bottom panel as RNA loading control.

Figure 17:
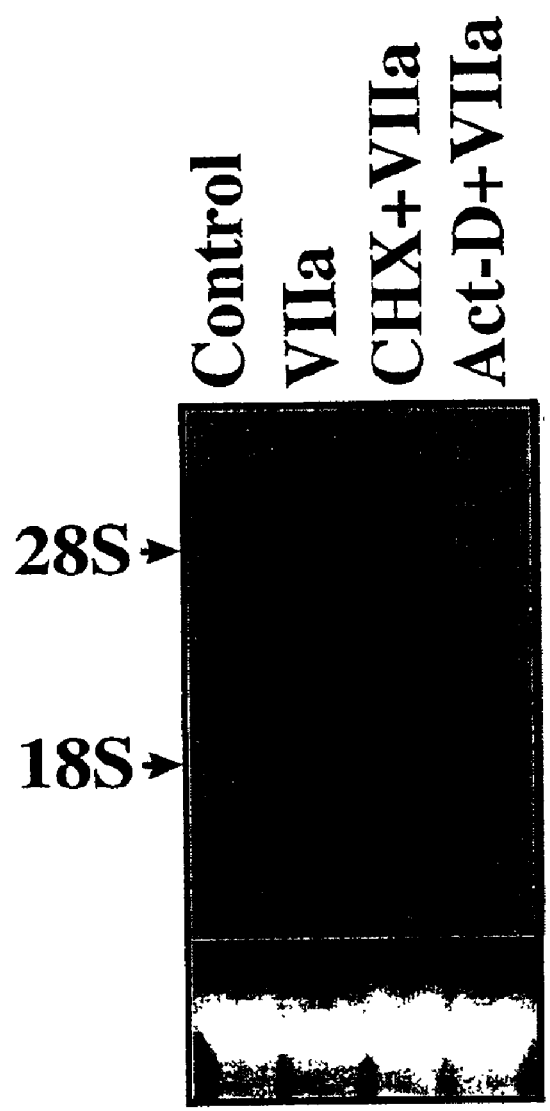

FIG. 17. Effect of actinomycin-D and cycloheximide on factor VIIa-induced Cyr61 mRNA steady-state levels. Quiescent monolayers of WI-38 cells were preincubated with a control vehicle, actinomycin D (10 μg/ml) or cycloheximide (10 μg/ml) for 30 min before the cells were exposed to factor VIIa (5 μg/ml) for 45 min. Total RNA (10 μg) was patiented to Northern blot analysis and probed with radiolabeled Cyr61. Ethidium bromide staining of 28S ribosomal RNA of the corresponding blot is shown in the bottom panel as RNA loading control.

Figure 18A:
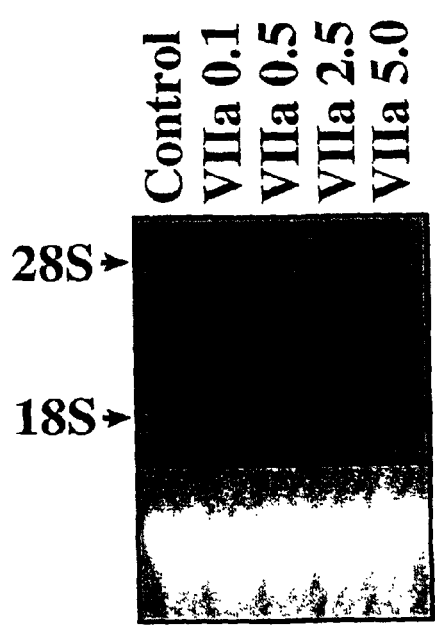
Figure 18B:
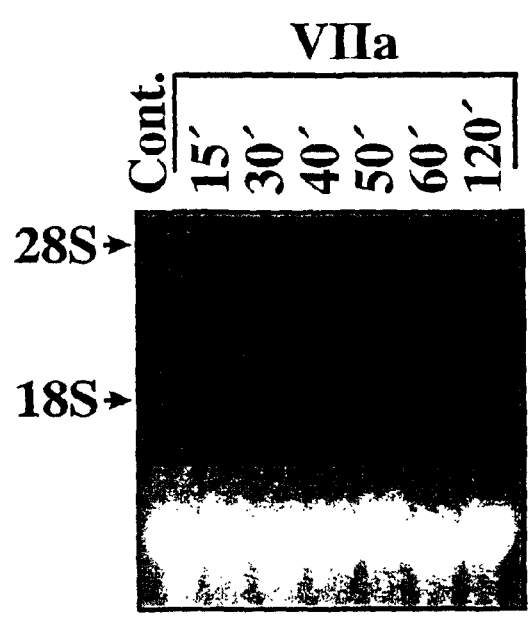

FIGS. 18A and 18B. Factor VIIa induces the expression of CTGF. Quiescent monolayers of WI-38 cells were treated with factor VIIa (5 μg/ml) for varying time periods. Total RNA (10 μg) was patiented to Northern blot analysis and probed with radio labeled CTGF. Ethidium bromide staining of 28S ribosomal RNA of the corresponding blot is shown as RNA loading control.

DETAILED DESCRIPTION OF THE INVENTION

The present invention relates to the use of FVII or FVIIa or another TF agonist for the manufacture of a pharmaceutical composition for inducing or enhancing cell migration.

In a further aspect the present invention relates to the use of FVII, FVIIa or another TF agonist for the manufacture of a pharmaceutical composition for inducing or enhancing wound healing or angiogenesis.

In a still further aspect the present invention relates to the use of FVIIai or another TF antagonist for the manufacture of a pharmaceutical composition for inhibiting or preventing cell migration.

In one embodiment the cell migration is in a subject.

In a further aspect the present invention relates to the use of FVIIai or another TF antagonist for the manufacture of a pharmaceutical composition for inhibiting or preventing angiogenesis, metastasis, tumour growth or tumour invasion.

In a further aspect the present invention concerns a method for inducing or enhancing cell migration in a patient, which comprises administering an effective amount of FVII or FVIIa or another TF agonist to said patient.

In a still further aspect the present invention concerns a method for inhibiting or preventing cell migration in a patient, which comprises administering an effective amount of FVIIai or another TF antagonist to said patient.

In a particular embodiment the effective amount is a daily dosage from about 5 μg/kg/day to about 500 μg/kg/day.

In a further embodiment the TF antagonist comprises a modified FVIIa, for example, FFR-FVIIa.

The present invention provides a mechanism for an activity of FVII and/or FVIIa that relates to stimulation of cell migration. Such a mechanism provides the basis for establishing the involvement of FVII and/or FVIIa in pathological conditions in which TF expressing cells like endothelial cells, epithelial cells, fibroblasts, smooth muscle cells and monocytes/macrophages participate. The invention furthermore provides the basis for identifying specific pharmacological targets that are useful for therapeutic intervention.

Thus, the present invention relates to usage of FVII and/or FVIIa and/or FVIIai in therapeutic treatment of pathological conditions that can be related to cell migration or treated by specific regulation of cell migration.

In another aspect, the present invention relates to a method of detecting drug candidates that regulate cell migration, which method comprise
a) culturing a TF expressing cell;
b) measuring the migration of the cell;
c) incubating the cell with a drug candidate, and
d) measuring the migration of the incubated cell and determining any change in the level of migration compared to the migration measured in step b, such change being indicative of biologically active drug candidate in said cell.

Generally, the blood components, which participate in what has been referred to as the coagulation "cascade" are proenzymes or zymogens, enzymatically inactive proteins, which are converted to proteolytic enzymes by the action of an activator, itself an activated clotting factor. Coagulation factors that have undergone such a conversion and generally referred to as "active factors", and are designated by the addition of the letter "a" to the name of the coagulation factor (e.g. factor VIIa).

The term "zinc-chelator" is intended to comprise a compound that binds to factor VIIa and induces replacement of calcium ions with zinc ions within factor VIIa, thereby inhibiting the activity of factor VIIa or tissue factor-factor VIIa complex (TF-FVIIa).

A suitable TF antagonist according to the invention may be a zinc-chelating compound, e.g. a dihydroxamate or a dihydrazide with the hydroxamate or hydrazide groups located relative to each other in such a position that they are able to chelate a zinc ion. The zinc-chelating compound acts in combination with FVIIa. $Zn^{2+}$-ions exert their inhibitory action in competition with a stimulatory effect of $Ca^{2+}$-ions. It is predicted that $Zn^{2+}$-ions displace $Ca^{2+}$-ions from one or more calcium binding site(s) within FVIIa. Zinc-chelating compounds, e.g. hydroxamates and hydrazides, are capable of acting as powerfull supporters for binding of zinc ions in competition with calcium ions. Specific compounds thereby potentiate zinc inhibition of the activity of the factor VIIa/tissue factor complex. The activity of factor VIIa in complex with tissue factor can be inhibited by a mechanism in which a zinc chelator binds to factor VIIa and facilitates replacement of $Ca^{2+}$ with $Zn^{2+}$. By this action the chelator exerts a modulatory effect on TF at the normal concentration of free $Ca^{2+}$ and $Zn^{2+}$ ions in the blood.

The term "FVII" or "factor VII" means "single chain" (zymogenic) coagulation factor VII. The term "Factor VIIa", or "FVIIa" means "two chain" activated coagulation factor VII cleaved by specific cleavage at the Arg152-Ile153 peptide bond. FVII and FVIIa may be purified from blood or produced by recombinant means. It is evident that the practice of the methods described herein is independent of how the purified factor VIIa is derived and, therefore, the present invention is contemplated to cover use of any factor VII or FVIIa preparations suitable for use herein. Preferred are human FVIIa. FVII or FVIIa is also intended to include FVII variants wherein one or more amino acid residues has (have) been replaced.

The term "modified factor VII", "inactivated FVII" or "FVIIai" is intended to mean FVIIa having at least one modification in its catalytic centre, which modification substantially inhibits the ability of modified FVIIa to activate FX and FIX. The terms may be used interchangeably. Such modification includes amino acid substitution (or replacement) of one or more of the catalytic triad residues Ser344, Asp142 and His193, and also includes modification of catalytic triad residues with serine protease inhibitors such as organo-phosphor compounds, sulfanylfluoride, peptide halomethyl ketone or azapeptide. FFR-FVIIa is one example of a FVIIai derivative obtained by blocking of the active centre of FVIIa with the irreversible inhibitor, D-phenylalanine-L-phenylalanine-L-argininine chloromethyl ketone (FFR cmk). Other suitable FVIIai derivates are inactivated FVIIa obtained or obtainable by blocking the active centre with L-phenylalanine-L-phenylalanine-L-argininine chloromethyl ketone, dansyl-L-phenylalanine-L-phenylalanine-L-argininine chloromethyl ketone, or dansyl-D-phenylalanine-L-phenylalanine-L-argininine chloromethyl ketone, Preferred is FFR-FVIIa (FVIIa inactivated by FFR cmk).

The term "protein kinase" is intended to indicate an enzyme that is capable of phosphorylating serine and/or threonine and/or tyrosine in peptides and/or proteins.

The term "drug candidate" is intended to indicate any sample, which has a biological function or exerts a biological effect in a cellular system. The sample may be a sample of a biological material such as a microbial or plant extract, or it may be a sample containing a compound or mixture of compounds prepared by organic synthesis or genetic techniques.

The term "TF agonist" comprises compounds inducing
a) signal transduction by direct binding to TF (e.g. FVIIa),
b) stimulation of MAPK cascade,
c) abrogation of MAPK inhibition (e.g. PTPase inhibitors),
which agonists are drug candidates as defined above.

The term "TF antagonist" comprises
a) reagents which compete with FVIIa for binding to TF without transmission, e.g. FVIIai,
b) reagents which bind to FVIIa and prevent binding to TF, e.g. Zn hydroxamate,
c) reagents which inhibit signal transduction by interfering with members of the MAPK cascade,
d) reagents which bind to FVIIa/TF and prevent transmission,
e) reagents which bind to FVIIa/TF/FX and prevent transmission,
f) reagents which block human factor X activation catalysed by human tissue factor/factor VIIa complex,
which antagonists are drug candidates as defined above.

The term "pharmacological targets" is intended to indicate a protein that can alter the migration of TF expressing cells.

The term "reporter gene" is intended to indicate a DNA construct that, when transcribed, produces a protein that can be detected.

The term "SRE promoter element" means a DNA sequence that binds transcription factors induced by components present in serum.

The term "TF expressing cell" means any mammalian cell that expresses TF.

The term "protein phosphorylation" is intended to indicate phosphorylation of serine and/or threonine and/or tyrosine in peptides and/or proteins.

Modulation or regulation of cell migration is defined as the capacity of FVIIa or another TF agonist, or FVIIai or another TF antagonist to 1) either increase or decrease ongoing, normal or abnormal, cell migration, 2) initiate normal cell migration, and 3) initiate abnormal cell migration.

Modulation or regulation of gene expression encompasses the capacity of FVIIa or another TF agonist, or FVIIai or another TF antagonist to 1) either increase or decrease ongoing, normal or abnormal, cell migration, 2) initiate normal cell migration, and 3) initiate abnormal cell migration.

Modulation or regulation of gene expression encompasses an increase or decrease in any parameter of gene expression of at least about 1.5-fold, preferably at least about 2-fold, more preferably at least about 3-fold, and most preferably at least about 5-fold. Useful parameters of gene expression include, without limitation, rate of transcription, level of mRNA accumulation, rate of synthesis of the gene product, and level of protein accumulation. Modulation of gene expression may also be reflected in secondary indices known to those of ordinary skill in the art. Any measurable change in any of these parameters indicates regulation of expression.

In this context, the term "treatment" is meant to include both prevention of an adverse condition and regulation of an already occurring condition with the purpose of inhibiting or minimising the condition. Prophylactic administration of FVIIa or another TF agonist, or FVIIai or another TF antagonist is thus included in the term "treatment".

In this context, the term "one unit" is defined as the amount of factor VII present in 1 ml of normal plasma, corresponding to about 0.5 µg protein. After activation 50 units correspond to about 1 µg protein.

In this context, the term "patient" is defined as any animal, in particular mammals, such as humans. The term "subject" is used interchangeably with "patient"

ABBREVIATIONS

TF tissue factor
FVII factor VII in its single-chain, unactivated form
FVIIa factor VII in its activated form
RFVIIa recombinant factor VII in its activated form
FVIIai modified (inactivated) factor VII
FFR-FVIIai factor VII inactivated by reaction with D-Phe-L-Phe-L-Arg chloromethyl ketone Tissue factor (TF) is the cellular receptor for factor FVIIa (FVIIa) and the complex is principal initiator of blood coagulation. We have studied the effects of FVIIa binding to TF on cell migration and signal transduction of human fibroblasts that express high amounts of TF. Fibroblasts incubated with FVIIa migrated towards a concentration gradient of PDGF-BB at about one hundred times lower concentration than do fibroblasts not ligated with FVIIa. Anti-TF antibodies inhibited the increase in chemotaxis induced by FVIIa/TF. Moreover, a pronounced suppression of chemotaxis induced by PDGF-BB was observed with active site-inhibited FVIIa (FFR-FVIIa). The possibility was excluded that hyperchemotaxis was induced by a putative generation of FXa and thrombin activity.

FVIIa induced the production of inositol-1,4,5-trisphosphate to the same extent as PDGF-BB; the effects of FVIIa and PDGF-BB were additive. FFR-FVIIa did not induce any release of inositol-1,4,5,-trisphosphate. The cellular migration response to PDGF-BB and FVIIa was totally blocked by a PLC-inhibitor, suggesting that activation of PLC is important for the response. Thus, binding of FVIIa to TF can independent of coagulation, modulate cellular responses, such as chemotaxis, and the catalytic activity of FVIIa is necessary.

TF is believed to exert a function in tumour cell metastasis, but the mechanism is yet not known. However, Ott et al. very recently identified actin-binding protein 280 (ABP-280) as a ligand for the TF cytoplasmic domain, providing a molecular pathway by which TF may support tumor cell metastasis. The molecular signals and the biological functions transduced by FVIIa/TF are, however, still poorly understood.

Human fibroblasts have a constitutive expression of TF. These cells also express receptors for platelet-derived growth factor (PDGF). PDGF induces in its target cells mitogenicity, actin reorganization and directed cell migration (chemotaxis). We have previously shown that PDGF-BB is an efficient chemotactic factor for human fibroblasts and that the chemotactic response is mediated by the β-receptor class. Therefore, these cells were chosen to study putative signal transduction and cell migration induced by binding of FVIIa to TF.

Below we show for the first time a clear connection between signalling induced by FVIIa binding to TF and the cellular response to a growth factor. We present data that in human fibroblasts the FVIIa/TF complex leads to a hyperchemotactic response to PDGF-BB. Furthermore, active site-inhibited FVIIa (FFR-FVIIa) in a dose-dependent way suppressed the directed migration towards PDGF-BB. By the use of specific inhibitors to PLC and phosphatidylinositol 3'-kinase (PI3'-kinase) we also demonstrate that the hyperchemotactic response towards PDGF-BB induced by FVIIa/TF signalling is dependent upon phospholipase C (PLC) activity but independent of PI3'-kinase. FVIIa and PDGF-BB induced the production of inositol-1,4,5-trisphosphate ($IP_3$), one of the second messengers released after activation of PLC, in an additive manner.

TF is constitutively expressed on the plasma membrane of many extravascular cells, such as stromal fibroblasts in vascular adventitia and in fibrous capsules of liver, spleen and kidney. Thus, expression of TF is found at sites physically separated from the circulating blood and providing a haemostatic envelope. Upon injury this barrier is thought to protect the organism against bleeding. TF can, however, be induced in monocytes/macrophages, vascular smooth muscle cells, endothelial cells and in a number of tumour cells by a variety of agents, including cytokines and growth factors. Induction at the transcriptional level occurs rapidly after stimulation, identifying TF as a growth-related immediate early gene.

In this study we have investigated the role of TF as a signalling receptor. We show that human fibroblasts with a constitutive expression of TF upon ligand binding of FVIIa migrate towards extremely low concentrations of PDGF-BB. TF/FVIIa alone did not induce enhanced spontaneous migration, i.e. random migration. Thus, a combination of intracellular signal transduction by FVIIa/TF and the growth factor PDGF-BB was necessary to achieve the motility response. Not only binding to TF, but also the catalytic activity of TF/FVIIa was mandatory, since active-site inhibited FVIIa did not elicit enhanced migration response. Furthermore, inhibitory monoclonal antibodies prevented enhancement of the chemotactic response by FVIIa. We also excluded that indirect signalling occurred due to FXa or thrombin, since TAP and Hirudin had no effect on FVIIa/TF induced chemotaxis. We instead found that increasing concentrations of FFR-FVIIa actively inhibited PDGF-BB induced chemotaxis. Fibroblasts incubated with FFR-FVIIa showed completely normal random migration. The inhibitory effect of FFR-FVIIa on PDGF-BB-induced chemotaxis was not observed in the presence of the combination of anti-TF antibodies thereby ruling out the possibility of FFR-FVIIa being toxic. The results suggest rather, that in cells expressing PDGF β-receptors and TF, the FVIIa/TF complex is of importance for the chemotactic response to PDGF-BB.

Our finding that FVIIa increases $IP_3$ production, and the previously reported data on FVIIa/TF induced $Ca^{2+}$ oscillations especially in MDCK cells, strongly support the notion that PLC is activated by FVIIa/TF signalling in a number of cells. In addition, the hyperchemotactic response in human fibroblasts to PDGF-BB induced by FVIIa/TF was blocked in a dose-dependent way by a PLC-inhibitor. We have previously found a similar hyperchemotactic response to PDGF-BB in PDGF β-receptor Y934F mutant cells, which showed increased phosphorylation and activation of PLC-γ1. In these cells, the enhanced phosphorylation of PLC-γ1 correlated with a threefold higher $IP_3$ production compared to wild-type PDGF β-expressing cells. The combination of FVIIa/TF and PDGF-BB induced about twofold increase in $IP_3$ production in human fibroblasts. FVIIa/TF-induced $IP_3$ production, however, did not correlate with phosphorylation of PLC-γ1. Tyrosine phosphorylation of PLC-γ2 induced by FVIIa/TF cannot be excluded, but seems unlikely since the expression of PLC-γ2 is very low in human fibroblasts. Moreover, the intracellular part of TF is not endowed with intrinsic protein tyrosine kinase activity. These results suggest that FVIIa/TF induces activation of β and/or δ PLC isozymes. In the assay for $IP_3$ release the cell culture medium was supplemented with 0.1% FBS containing only about 0.1 nM FXa. We found that a concentration of more than 20 nM FXa is necessary to induce $IP_3$ production. The mechanism by which β or δ PLC isozymes are activated remains to be elucidated. It is believed that activation involves the cooperation between TF and a membrane-associated protein.

Lately, the connection of TF with the cytoskeleton was identified. A molecular interaction between the cytoplasmatic domain of TF and the actin filament-binding protein ABP 280 was shown. Furthermore, TF was found to be in close contact with actin and actin filament-binding proteins, such as α-actinin and ABP280 in lamellipodia and ruffled membrane areas in spreading epithelial cells. ABP 280, a member of the filamin subfamily, is required for normal function of lamellipodia and thus highly important for cell motility. PI3'-kinase and PLC isozymes are implicated in chemotactic responses, such as mobilisation of actin-binding proteins. In previous studies we observed that the PI3'-kinase pathway in PDGF-β receptor induced chemotaxis seems less important in cells with over-expression and enhanced activity of PLC-γ1. This was also the case for cells with FVIIa bonded to TF. This indicates that the magnitude of activation of PI3'-kinase and PLC isozymes will determine which of these pathways will dominate. Taken together, our data show that cell migration is an important morphogenic function induced by FVIIa/TF signalling.

Chemotaxis plays a pivotal role in wound healing, angiogenesis and metastasis. Chemotaxis is also an important component in the development of atherosclerotic plaques. In these processes a variety of cells express TF as well as PDGF and PDGF receptors. Restenosis is a major complication following interventional procedure of obstructed arteries. PDGF has been implicated in the vessel wall's response (neointima formation) to mechanical injury by mediating the migration and proliferation of smooth muscle cells and fibroblasts. We have shown now for the first time that FVIIa binding to TF-expressing cells have an increased chemotactic response to PDGF, which is independent of the coagulation.

At present, not much is known about signaling pathway(s) that are induced by proteolytically active VIIa and how the signals generated by VIIa could contribute to cellular processes. One possibility is that FVIIa could induce the expression of growth regulators that act downstream to induce cellular processes. To investigate this possibility, in the present study, we have examined changes in the transcriptional program in human fibroblasts in response to exposure to VIIa using a cDNA microarray that contain more than 8,000 individual human genes. We chose fibroblasts since these cells normally encounter serum, which contain growth factors and activated clotting factors in the context of vascular injury due to physical (e.g., surgery) and pathophysiological conditions. The temporal program of gene expression observed in response to serum suggests that fibroblasts are programmed to interpret the abrupt exposure to serum nor as a general mitogenic stimulus but as a specific physiological signal. Characterization of transcriptional activation in response to serum and growth factors also suggest that fibroblasts are an active participant in a conversation among the diverse cells which collectively control inflammation, angiogenesis and wound healing.

cDNA microarray analysis with mRNA isolated from fibroblasts exposed to VIIa for 90 min shows upregulation of Cyr61. Northern blot analysis confirmed the VIIa-induced expression of Cyr61 in fibroblasts. Although not as robust as in fibroblasts, VIIa also increases the expression of Cyr61 in vascular smooth muscle cells. Induction of Cyr61 expression is dependent on the FVIIa's catalytic activity since FVIIai fail to induce the expression of Cyr61. Although factor Xa and thrombin could also induce the expression of Cyr61 (data not shown), these compounds are not involved in FVIIa-induced expression of Cyr61. We found no evidence for the generation of traces factor Xa and thrombin in our experimental system. Further, specific inhibitor of factor Xa and thrombin had no significant effect on the FVIIa-induced expression of Cyr61.

Cyr61 is an immediate-early gene that is transcriptionally activated by serum growth factors in fibroblasts. It encodes a secreted 40 kDa, cysteine-rich and heparin-binding protein that associates with extracellular matrix and cell surfaces. Cyr61 is a member of an emerging gene family of conserved and modular proteins characterized by the presence of an N-terminal secretory signal, followed by four modular structural domains and 38 cysteine residues that are largely conserved among members of the family. The protein family now consists of six distinct members, including Cyr61, connective tissue growth factor (CTGF) and an avian proto-oncoprotein, Nov (thus named as CCN family) (The CCN family is further described in Lau et al., Exp. Cell Res 248: 44-57, 1999). Cyr61 protein is shown to (i) promote the attachment and spreading of endothelial cells in a manner similar to that of fibronectin, (ii) enhance the effects of bFGF and PDGF on the rate of DNA synthesis of fibroblasts and vascular endothelial cells (iii) promotes cell migration in both fibroblasts and endothelial cells. Recent studies show that Cyr61 acts as a ligand to integrin $α_vβ_3$, an adhesion receptor known to be involved in signaling that regulates a number of cellular processes including angiogenesis and tumor metastasis. Purified Cyr61 protein was shown to stimulate directed migration of human microvascular endothelial cell in culture through a $α_vβ_3$-dependent pathway and induce neovascularization in rat corneas. Furthermore, expression of Cyr61 in tumor cells promotes tumor growth and vascularization.

Based on the present data that show FVIIa induces Cyr61 expression in fibroblasts, it is believed that FVIIa-induced Cyr61 is responsible, acting through integrin $α_vβ_3$, for FVIIa-mediated cell migration and tumor metastasis. Thus, Cyr61 links FVIIa-TF proteolytical signal to the integrin-signaling pathway. The observations that VIIa catalytic activity is required for migration of smooth muscle cells and tumor cells, and tumor metastasis are consistent with the other observation that FVIIa catalytic activity is required for the induction of Cyr61.

In addition to Cyr61, VIIa could also induce other regulators that could mediate FVIIa-induced biological responses. FVIIa binding to cell surface TF in pancreatic cancer cells was shown to selectively over-express uPAR gene. Earlier we have shown, using differential display technique, up-regulation of transcription of poly(A)polymerase gene in fibroblasts exposed to FVIIa. Although it would have been interesting to find out whether the cDNA microarray also show differential expression of PAP, the filter did not contain the PAP cDNA. In addition to Cyr61, our cDNA microarray also show differential expression of four other genes (see results), but the differential expression ratio was very close to the borderline significance. Since in preliminary experiments we could not confirm their differential expression by Northern blot analysis and also the absence of any suggestive relevant data on the ability of these gene products to mediate FVIIa-induced biological responses, we did not analyze their expression further. However, since CTGF is a structurally related molecule to Cyr61 and elicit same biological responses as Cyr61, we have examined the expression of CTGF even though the relative ratio of CTGF expression in FVIIa-treated sample vs the control sample in the cDNA microarray is 1.8 (2 is a conservative estimate to be a real magnitude in the assay). The data revealed that FVIIa also induced the expression of CTGF and the kinetics of VIIa-induced expression of CTGF was similar to that of Cyr61.

Although CTGF behaves very similar to Cyr61, subtle differences exist between them. For example, (a) CTGF has shown to be mitogenic in itself whereas Cyr61 has no intrinsic mitogenic activity but augments growth factor-induced DNA synthesis (b) Cyr61 stimulates chemotaxis whereas CTGF stimulates both chemotaxis and chemokinesis (c) although both Cyr61 and CTGF are ECM-associated signalling molecules, CTGF is shown to secrete into culture medium. Thus, it is possible that FVIIa regulates cellular functions locally via Cyr61 whereas acts at a distance from its site through the secretion of CTGF.

The regimen for any patient to be treated with FVIIa or another TF agonist or FVIIai or another TF antagonist as mentioned herein should be determined by those skilled in the art. The daily dose to be administered in therapy can be determined by a physician and will depend on the particular compound employed, on the route of administration and on the weight and the condition of the patient. An effective amount is suitably a daily dosage from about 5 µg/kg/day to about 500 µg/kg/day, preferably from about 10 µg/kg/day to 300 µg/kg/day, more preferred from about 15 µg/kg/day to 200 µg/kg/day, most preferred from about 20 µg/kg/day to 100 µg/kg/day.

The FVIIa or another TF agonist or FVIIai or another TF antagonist should be administered in one single dose, but it can also be given in multiple doses preferably with intervals of 4-6-12 hours depending on the dose given and the condition of the patient.

The FVIIa or another TF agonist or FVIIai or another TF antagonist may be administered intravenously or it may be administered by continuous or pulsatile infusion or it may be administered directly to the relevant site such as, for example, injected directly into a tumour. FVIIa or another TF agonist or FVIIai or another TF antagonist is preferably administered by intraveneous injections and in an amount of about 100-100,000 units per kg body weight, and preferably in an amount of about 250-25,000 units per kg body weight corresponding to about 5-500 µg/kg, a dose that may have to be repeated 2-4 times per 24 hours.

Conventional techniques for preparing pharmaceutical compositions, which can be used according to the present invention are, for example, described in *Remington's Pharmaceutical Sciences*, 1985.

The compositions used according to this invention are prepared by methods known per se by the skilled artisan.

In short, pharmaceutical preparations suitable for use according to the present invention is made by mixing FVII, FVIIa or another TF agonist or FVIIai or another TF antagonist, preferably in purified form, with suitable adjuvants and a suitable carrier or diluent. Suitable physiological acceptable carriers or diluents include sterile water and saline. Suitable adjuvants, in this regard, include calcium, proteins (e.g. albumins), or other inert peptides (e.g. glycylglycine) or amino acids (e.g. glycine, or histidine) to stabilise the purified factor VIIa. Other physiological acceptable adjuvants are non-reducing sugars, polyalcohols (e.g. sorbitol, mannitol or glycerol), polysaccharides such as low molecular weight dextrins, detergents (e.g. polysorbate) and antioxidants (e.g. bisulfite and ascorbate). The adjuvants are generally present in a concentration of from 0.001 to 4% w/v. The pharmaceutical preparation may also contain protease inhibitors, e.g. apronitin, and preserving agents.

The preparations may be sterilised by, for example, filtration through a bacteria-retaining filter, by incorporating sterilising agents into the compositions, by irradiating the compositions, or by heating the compositions. They can also be manufactured in the form of sterile solid compositions, which can be dissolved in sterile water, or some other sterile medium suitable for injection prior to or immediately before use.

In different aspects the present invention concerns:

A method of regulating the expression of at least one gene in a cell, comprising the steps of:
 a) contacting said cell with factor VII (a) or a tissue factor antagonist
 b) determining the expression of said gene in said cell.

The above method, wherein said cell is a human vascular cell expressing tissue factor, including fibroblasts and smooth muscle cells.

The method, wherein said gene is selected from the group consisting of Cyr61, CTFG, dopamine D2 receptor, EST Incyte PD 395116 or P2U nucleotide receptor.

The method, wherein said tissue factor antagonist is modified factor VII (a) known as factor VIIai.

A method wherein the expression of said gene is enhanced.

A method wherein the expression of said gene is inhibited or minimized.

A method of enhancing the expression of said gene comprising contacting the cell with factor VIIa.

A method of inhibiting the expression of said gene comprising contacting the cell with modified factor VII known as FVIIai.

The method wherein said gene is EST PD674714.

A method for regulating cell migration, comprising the steps of:
 a) contacting said cell with factor VIIa or a tissue factor antagonist;
 b) determining the migration of said cell.

The method, wherein said cell is a human cell expressing tissue factor, including fibroblasts, smooth muscle cells, tumour cells, haematopoietic cells and epithelial cells.

The method, wherein the tissue factor antagonist is modified factor VIIa known as factor VIIai.

The method, wherein the modified factor VII is selected from Dansyl-Phe-Pro-Arg chloromethyl ketone, Dansyl-Glu-Gly-Arg chloromethyl ketone, Dansyl-Phe-Phe-Arg chloromethyl ketone and Phe-Phe-Arg chloromethylketone.

A method of enhancing cell migration, comprising contacting the cell with FVIIa or a tissue factor agonist.

A method of reducing or inhibiting cell migration, comprising contacting the cell with a tissue factor antagonist.

A method for inducing or enhancing wound healing in a patient, comprising administering to said patient an effective amount of a pharmaceutical composition comprising Factor VIIa or a tissue factor agonist.

A method for inhibiting the invasiveness of tumour cells comprising contacting said cells with an effective amount of a tissue factor antagonist.

A method for inhibiting cell migration, invasion, migration-induced cell proliferation or angiogenesis in a patient having a disease or condition associated with undesired cell migration, invasion, migration-induced cell proliferation or angiogenesis, comprising administering to said patient an effective amount of a pharmaceutical composition comprising a tissue factor antagonist.

The method, wherein the disease or condition is primary tumour growth, tumour invasion or metastasis.

The method, wherein the tissue factor antagonist is modified factor VII known as FVIIai.

Use of factor VIIa or a tissue factor antagonist for the manufacture of a medicament for regulating cell migration.

Use, wherein factor VIIa is used for the manufacture of a medicament for enhancing cell migration.

Use, wherein a tissue factor antagonist is used for the manufacture of a medicament for reducing or inhibiting cell migration.

The method, wherein the tissue factor antagonist is modified factor VIIa known as factor VIIai.

Use, wherein the modified factor VII is selected from Dansyl-Phe-Pro-Arg chloromethyl ketone, Dansyl-Glu-Gly-Arg chloromethyl ketone, Dansyl-Phe-Phe-Arg chloromethyl ketone and Phe-Phe-Arg chloromethylketone.

The present invention is further illustrated by the following examples that, however, are not to be construed as limiting the scope of protection. The features disclosed in the foregoing description and in the following examples may, both separately and in any combination thereof, be material for realising the invention in diverse forms thereof.

EXAMPLES

Example 1

Preparation of FVII

Human purified factor VIIa suitable for use in the present invention is preferably made by DNA recombinant technology, e.g. as described by Hagen et al., *Proc.Natl.Acad.Sci. USA* 83: 2412-2416, 1986 or as described in European Patent No. 200.421 (ZymoGenetics). Factor VIIa produced by recombinant technology may be authentic factor VIIa or a more or less modified factor VIIa provided that such factor VIIa has substantially the same biological activity for blood coagulation as authentic factor VIIa. Such modified factor VIIa may be produced by modifying the nucleic acid sequence encoding factor VII either by altering the amino acid codons or by removal of some of the amino acid codons in the nucleic acid encoding the natural FVII by known means, e.g. by site-specific mutagenesis.

Factor VII may also be produced by the methods described by Broze and Majerus, *J.Biol.Chem.* 255 (4): 1242-1247, 1980 and Hedner and Kisiel, *J.Clin.Invest.* 71: 1836-1841, 1983. These methods yield factor VII without detectable amounts of other blood coagulation factors. An even further purified factor VII preparation may be obtained by including an additional gel filtration as the final purification step. Factor VII is then converted into activated FVIIa by known means, e.g. by several different plasma proteins, such as factor XIIa, IX or Xa. Alternatively, as described by Bjoern et al. (Research Disclosure, 269 September 1986, pp. 564-565), factor VII may be activated by passing it through an ion-exchange chromatography column, such as Mono Q® (Pharmacia fine Chemicals) or the like.

Example 2

Preparation of FVIIai

Modified factor VII suitable for use in the present invention is made, e.g. as described in International Publications Nos. 92/15686, 94/27631, 96/12800 and 97/47651 ZymoGenetics/Novo Nordisk).

Example 3

Effects of FVIIa and FFR-FVIIa on the Chemotactic Response of Fibroblasts to PDGF-BB Fibroblasts expressing active TF (FIG. 1A and FIG. 1B) were incubated with 100 nM of FVIIa and seeded in the upper part of the modified Boyden chamber; while media containing 10% FBS and PDGF-BB at different concentrations were added below the 150 µm micropore filter. The migration of the cells under conditions where medium containing 10% FBS without PDGF-BB was added below the filter was used as a measure of random migration, and calculated as 100% migration. A significant migration response was recorded at a concentration of 0.01 ng/ml PDGF-BB in cells stimulated by FVIIa compared to 1 ng/ml PDGF-BB for cells not ligated with FVIIa, i.e. a 100-fold difference in concentration (FIG. 2). At 0.01-0.1 ng/ml PDGF-BB the migration response to FVIIa increased dose dependently, starting at 25 nM and with a maximal effect at 50-100 nM FVIIa (FIG. 3A-D). No enhancement of random migration was observed after activation with FVIIa. To test whether the proteolytically active FVIIa was mandatory for the hyperchemotactic response to PDGF-BB, fibroblasts were also incubated with 100 nM FFR-FVIIa and assayed in the Boyden chamber in the same way (FIG. 2). No increased chemotaxis was observed with FFR-FVIIa at low concentrations of PDGF-BB, 0.01-1 ng/ml. In contrast, a pronounced suppression of chemotaxis induced by 10-50 ng/ml PDGF-BB was achieved by 100 nM FFR-FVIIa (FIGS. 2 and 3A-D).

When fibroblasts were preincubated with a mixture of three different TF antibodies and then with FVIIa or FFR-FVIIa, the migration response to PDGF-BB was identical to the response of Fibroblasts without the presence of ligand bonded to TF (FIG. 4). An irrelevant monoclonal IgG antibody did neither prevent hyperchemotaxis induced by FVIIa nor the inhibition of the migration response induced by FFR-FVIIa (data not shown). The presence of the IgG antibodies or the three TF antibodies did not change random migration of the fibroblasts (data not shown).

Example 4

The Hyperchemotactic Response is not Mediated by FXa or by Thrombin

Since FVIIa-induced signal transduction leading to the hyperchemotactic response to PDGF-BB was dependent on the catalytic activity of FVIIa it was important to determine whether signaling occurred directly or via FXa or thrombin generated by the FVIIa/TF complex. The enhanced migration response transduced by FVIIa/TF was not blocked by 0.2-10 μM Tick anticoagulant peptide (TAP), which specifically blocks the active site of FXa and prevents a further activation of the coagulation cascade leading to thrombin formation (FIGS. 5A,5B). Neither addition of 5 U/ml Hirudin, a specific thrombin inhibitor, had any effect on FVIIa/TF induced hyperchemotaxis (FIG. 6). TAP and Hirudin did not influence the migration of fibroblast in response to PDGF without the presence of the ligand FVIIa (FIGS. 5A, 5B, 6). Thus, it is unlikely that the effect of FVIIa on chemotaxis is mediated via the activation of FX or thrombin.

Example 5

The Hyperchemotactic Response to PDGF-BB is Influenced by PLC-Dependent Pathways, but Independent of PI3'-Kinase.

Activation of PI3'-kinase has recently been shown to be important for PDGF β-receptor induced chemotaxis. Therefore, we investigated whether LY294002, a specific PI3'-kinase inhibitor, was able to block the chemotactic response induced by FVIIa/TF signaling. Fibroblasts were pretreated with LY294002 at indicated concentrations for 30 minutes at 37° C. before the addition of 100 nM FVIIa and assayed in the Boyden chamber as described. The concentration of PDGF-BB was kept constant at 0.1 ng/ml throughout the assay, i.e. a very low concentration at which FVIIa/TF induced a significant chemotactic response. LY294002 was present during the entire experiments. FIG. 7 shows that the migration response to PDGF-BB mediated by FVIIa/TF-signalling was unaffected by the inhibition of PI3'-kinase.

To investigate whether the FVIIa/TF-induced chemotactic response involved the activation of phosphatidylinositol specific phospholipase C (PLC), we preincubated the fibroblasts with different concentrations of U73122, a specific PLC-inhibitor, for 30 minutes at 37° C. before adding 100 nM FVIIa; the cells were then patiented to the chemotaxis assay in the presence of the inhibitor. A close analogue, U73343, without effects on PLC was used as negative control. The concentration of PDGF-BB was kept constant at 0.1 ng/ml also in these experiments. Pretreatment of the cells with the active PLC-inhibitor U73122 inhibited the hyperchemotacic response to 0.1 ng/ml PDGF-BB in a dose-dependent way, with a total inhibition at 1 μM (FIGS. 8A and 8B). No effect on chemotaxis was observed when the inactive analogue U73343 was used.

Example 6

FVIIa/TF Induce Activation of PLC

To further explore the importance of PLC activity for the hyperchemotactic response, we also analysed the direct effects of FVIIa/TF on PLC activity in fibroblasts. Activation of PLC leads to production of two second messengers, inositol-1,4,5-trisphosphate ($IP_3$) and diacylglycerol. Fibroblasts were incubated with myo [$^3$H] inositol overnight, and then with 100 nM FVIIa or FFR-FVIIa for 60 minutes, followed by incubation with or without PDGF-BB at indicated concentrations. Treatment with 100 nM FVIIa alone for 60 minutes induced $IP_3$ release in fibroblasts at the same level as 10 ng/ml and 100 ng/ml PDGF-BB alone did (FIG. 9). Moreover, the combination of 100 nM FVIIa and 10 ng/ml or 100 ng/ml PDGF-BB doubled the $IP_3$ release. The active site-inhibited FVIIa did not induce release of $IP_3$. These results clearly show that PLC is activated upon binding of FVIIa to TF.

Example 7

Phosphorylation of PLC-γ1 is not Enhanced by TF/FVIIa Signalling in Fibroblasts

In order to determine whether the PLC-γ1 isoform, which is activated by certain tyrosine kinase receptors, was responsible for the increased PLC activity induced by FVIIa/TF, tyrosine phosphorylation of PLC-γ1 was studied. Fibroblasts were incubated in the absence or presence of 100 nM FVIIa or FFR-FVIIa for one hour, followed by the stimulation with 0, 2, 10 or 100 ng/ml PDGF-BB. After 5 minutes of incubation, the cells were lysed and PLC-γ1 was immunoprecipitated, separated by SDS-PAGE and immunoblotted with antiphosphotyrosine antibodies. Whereas a significant increase in tyrosine phosphorylation of PLC-γ1 was recorded with increasing concentrations of PDGF-BB, addition of FVIIa alone to the fibroblasts did not induce any tyrosine phosphorylation of PLC-γ1 (FIG. 10). Moreover, the combination of FVIIa and PDGF-BB at different concentrations did not induce any further phosphorylation compared to stimulation with PDGF-BB alone (FIG. 10). FFR-FVIIa had no effect on PLC-γ1 tyrosine phosphorylation (FIG. 10). Thus, other PLC isoforms than PLC-γ1 are responsible for the increased PLC activity after FVIIa stimulation.

Example 8

Methods

Cell cultures. Human foreskin fibroblasts, AG1518 and AG1523 were grown to confluence in Eagle's MEM supplemented with 10% fetal bovine serum (FBS). Before use, the cells were detached by trypsinization (2.5 mg/ml for 10 min at 37° C.), washed in Hank's balanced salt solution, and resuspended in Eagle's MEM with 10% FBS or in Ham's medium supplemented with 0.1% FBS.

Proteins. Human FVIIa (Novo Nordisk A/S, Gentofte, Denmark), was expressed and purified as described[29]. FFR-FVIIa (Novo Nordisk) was obtained by blocking of FVIIa in the active site with D-Phe-L-Phe-L-Arg chloromethyl ketone. Recombinant Tick anticoagulant peptide (TAP) was kindly provided by Dr. P. Vlasuk, Corvas (San Diego, Calif.). Hirudin was purchased from Sigma. LY294002, U73122 and U73343 were obtained from Biomol (Plymouth Meeting, Pa.). Anti-TF monoclonal antibodies, TF8-5G9, TF9-5B7 and MTFH-1 (Morrissey, J. H., Fair, D. S., Edgington, T. S. Monoclonal antibody analysis of purified and cell-associated tissue factor. Thromb. Res. 52, 247-261 (1988)) was a kind gift of Dr. James H. Morrissey, Oklahoma Medical Research Foundation. The phosphotyrosine antibody, PY99 was from Santa Cruz, Calif.

Flow cytometry. The surface expression of TF was analysed by immunofluorescence with a flow cytometer (Coulter Epics XL-MCL, Beckman Coulter, Fullerton, Calif., Coulter Electronics, USA). The instrument was calibrated daily with Immuno-Check™ or Flow Check™ calibration beads (Coulter). For indirect immunofluorescence experiments AG1518 or AG1523 fibroblasts were washed twice with PBS containing 0.1% bovine serum albumin (BSA), incubated for 30 minut~ps on ice with a fluorescein-isothiocyanate (FITC)-labelled anti-human TF monoclonal antibody (4508CJ, American Diagnostica, Greenwich, Conn. USA). The anti-Aspergillus niger glucose oxidase monoclonal IgG1 (Dakopatts) was used as a negative control. Mean channel fluorescence intensity (MFI) and percentage of positive cells were determined for each sample.

Determination of TF activity. The procoagulant activity of TF was determined as described by Lindmark et al. (Lindmark, E., Tenno, T., Chen, J., Siegbahn, A. IL-10 inhibits LPS-induced human monocyte tissue factor expression in whole blood. *Br. J. Haematol.* 102, 597-604 (1998)). Briefly, aliquots containing $0.2 \times 10^5$ AG1518 or AG1523 fibroblasts were washed twice with PBS, placed in the wells of a 96-well microtitreplate (Nunc, Roskilde, Denmark). The procoagulant activity was measured in a two-stage amidolytic assay where a chromogenic substrate, S-2222 (Chromogenix, Mölndal, Sweden), is cleaved by FXa, which in turn is activated from FX by the TF/FVIIa complex. A reaction mixture containing final concentrations of 0.6 mM S-2222, 2 mM $CaCl_2$ and coagulation factors from the factor concentrate Prothromplex-T™ TIM4 (Baxter, Vienna, Austria) at a final concentration of 1 U/ml FVII and 1.2 U/ml FX, was added to the wells, and change in absorbance at 405 nm following a 30 minutes incubation at 37° C. was determined. The measurements were done in triplicate.

Chemotaxis assay. The migration response of fibroblasts was assayed by means of the leading front technique in a modified Boyden chamber, as previously described (Siegbahn, A., Hanimacher, A., Westermark, B., Heldin, C-H. Differential effects of the various isoforms of platelet-derived growth factor on chemotaxis of fibroblasts, monocytes, and granulocytes. *J. Clin. Invest.* 85, 916-920 (1990) and Nistér, M., Hammacher, A., Mellström, K., Siegbahn, A., Rönnstrand, L., Westermark, B., Heldin, C-H. A glioma-derived PDGF A chain homodimer has different functional activities from a PDGF AB heterodimer purified from human platelets. *Cell* 52, 791-799 (1988)). Micropore filters (pore size 8 µm) were coated with a solution of type-1 collagen at room temperature over night. The filters were air dried for 30 minutes immediately before use. Human foreskin fibroblasts AG1523, were grown to confluence in Eagle's MEM supplemented with 10% FBS. The cells were detached by trypsinization (2.5 mg/ml for 10 minutes at 37° C.) and suspended in Eagle's MEM with 10% FBS. The fibroblasts were incubated for 10 minutes with or without FVIIa or FFR-FVIIa before assay. One hundred microliters of the cell suspension ($2 \times 10^5$ cells/ml) was added above the filter of the Boyden chamber. PDGF-BB was diluted in assay media (Eagle's MEM with 10% FBS) and added below the filter in the chamber. The cells were incubated for 6 hours at 37° C. in a humidified chamber containing 95% air/5% $CO_2$. FVIIa or FFR-FVIIa were present during the entire experiment. The filters were then removed, fixed in ethanol, stained with Mayer's Hemalun, and mounted. Migration was measured as the distance of the two furthest migrating fibroblast nuclei of one high-power field (12.5×24) in focus. The migration distance in each filter was calculated as the mean of the readings of at least three different parts of the filter. Experiments were performed with two to four separate filters for each concentration of chemoattractant. For each set of experiments, the migration of fibroblasts toward the assay media served as control.

In cases when anti-TF monoclonal antibodies or inhibitors to coagulation factors, TAP and Hirudin, were used, cells were preincubated for 10 minutes with these agents, then with or without FVIIa or FFR-FVIIa before the chemotaxis assay was performed. Antibodies, TAP or Hirudin were also present during the entire chemotaxis experiment. In experiments where the effects on the migration response of different inhibitors, LY294002, U73122 or U73343, were tested, cells were preincubated for 30 minutes with the inhibitors at indicated concentrations, and the inhibitors were also present throughout the experiments.

Assay for release of inositol trisphosphate ($IP_3$). Six-well plates with semi-confluent cultures of AG1518 human fibroblasts, were incubated over night (approx. 20 hours) with 2 µCi of myo($^3$H) inositol (Amersham) in 2 ml Ham's F12 with 0.1% FBS. Medium was changed to Ham's F12 with 0.1% FBS (containing 2 mM $CaCl_2$) and 20 mM LiCl and the cells were incubated for 15 minutes at 37° C. Cells were then incubated in the absence or presence of 100 nM FVIIa or 100 nM FFR-FVIIa for one hour. PDGF-BB (0, 10 or 100 ng/ml) was added and the incubation was continued for 10 minutes at 37° C. The $IP_3$ assay was performed as previously described by Eriksson et al. (Eriksson, A., Nånberg, E., Rönnstrand, L., Engström, U., Hellman, U., Rupp, E., Carpenter, G., Heldin, C-H., Claesson-Welsh, L. Demonstration of functionally different interactions between phospholipase C-γ and the two types of platelet-derived growth factor receptors. *J. Biol. Chem.* 270, 7773-7781 (1995)).

Assay for agonist-induced PLC-γ1 phosphorylation. Semi-confluent cultures of AG1518 were serum starved overnight (approx. 20 hours) in medium containing 0.1% FBS, and then incubated in the absence or presence of 100 nM FVIIa or FFR-FVIIa for one hour followed by incubation with 0, 2, 10 or 100 ng/ml PDGF-BB for 5 minutes at 37° C. Cells were lysed and PLC-γ1 was precipitated, essentially as previously described (Hansen, K., Johnell, M., Siegbahn, A., Rorsman, C., Engström, U., Wernstedt, C., Heldin, C-H., Rönnstrand, L. Mutation of a Src phosphorylation site in the PDGF β-receptor leads to increased PDGF-stimulated chemotaxis but decreased mitogenesis. *EMBO J.* 15, 5299-5313 (1996)) with anti-PLC-γ1 antiserum generated by immunizing rabbits with a peptide corresponding to the carboxyterminus of bovine PLC-γ1 (Artega, C. L., Johnson, M. D., Todderud, G., Coffey, R. J., Carpenter, G., Page, D. L. Elevated content of the tyrosine kinase substrate phospholipase C-γ1 in primary human breast carcinomas. *Proc. Natl. Acad. Sci. USA* 88, 10435-10439 (1991). Samples were separated by SDS-PAGE and immunoblotted with the phophotyrosine antibody PY99.

Statistical analysis. Data were analysed using the Statistica™ for Windows package (StatSoft, Tulsa, Okla. USA). A Student's t-test for dependent samples was used to determine statistical significance between different data sets. P values of <0.05 were considered statistically significant.

Proteins. Recombinant human VIIa, a gift from Novo Nordisk (Gentofte, Denmark), was reconstituted in sterile water at a concentration of 1 to 1.3 mg/ml. The stock VIIa solutions were checked for contaminating trace levels of endotoxin using limulus amebocyte lysate (Bio Whittaker) and none was detected (detection level 30 pg). Recombinant tick anticoagulant protein (TAP) was kindly provided by George Vlasuk (Corvas, San Diego, Calif.) and recombinant hirudin was obtained from either Sigma (St.Louis, Mo.) or Calbiochem (San Diego, Calif.). Purified human factor Xa and thrombin were, obtained from Enzyme Research Laboratories (Southbend, Ind.).

cDNA microarray. WI-38 cells were cultured to 80% confluency and serum deprived for 24 hours to enter quiescent state as described above. The culture medium was replaced with fresh serum-free DMEM (supplemented with 5 mM $CaCl_2$) and allowed to stabilize for 2 h in culture incubator. Then, the cells were treated with purified recombinant VIIa (5 µg/ml) for 90 min. At the end of 90 min treatment, total RNA was isolated from untreated (control) and VIIa-treated cells using Trizol (GIBCO BRL). Poly (A) RNA was purified by a double pass over Oligo Tex mRNA isolation columns as described in manufacturer's technical bulletin (Qiagen). Eight hundred ng (800 ng) of highly purified poly (A) RNA from the control and VIIa-treated cells were sent for cDNA microarray analysis service (Human UniGEM V microarray, Genome Systems Inc, St. Louis, Mo.).

Northern Blot Analysis. Total RNA was prepared using TRIZOL reagent from quiescent monolayer of WI-38 cells that were exposed to VIIa and other materials as described in Results. Northern blot analysis was carried out using standard procedure. Briefly, 10 µg of total RNA was size fractionated by gel electrophoresis in 1% agarose/6% formaldehyde gels and transferred onto the nitrocellulose membrane by a capillary blot method. Northern blots were prehybridized at 42° C. with a solution containing 50% formamide, 5×SSC, 50 mM Tris.HCl, pH 7.5, 0.1% sodium pyrophosphate, 1% SDS, 1% polyvinylpyrrolidone, 1% Ficoll, 25 mM EDTA, 100 µg/ml denatured salmon sperm DNA and 1% BSA and hybridized with $^{32}$P-labeled Cyr61 cDNA probe (106 cpm/ml). The hybridized membranes were exposed to either Dupont NEF or Fuji RX X-ray film. For quantification purposes, the membranes were exposed to phosphor screen for 1 to 4 h, and the exposed screens were analyzed in a PhosphorImger (Molecular Dynamics) using "Image-quant" software. To obtain mean values, the units (counts) obtained from different experiments were normalized to an internal control (counts present in control-treated sample).

Chromogenic Assay. WI-38 cells were cultured in 96-well culture plate and made them quiescent as described above. After washing the cells, FVIIa (5 µg/ml) in 1,00 µg of calcium containing buffer was added to the culture wells containing cells or wells coated with buffer (no cells). After 30 min incubation, 25 µg of chromogenic substrates for factor Xa and thrombin, i.e., Chromozym X and Chromozym TH were added to the wells. After 3 h of color development, the plate was read in a microplate reader. As controls, cells were incubated with trace concentrations of factor Xa (50 to 0.1 ng/ml) or thrombin (0.1 to 0.002 U/ml). No differences were found in absorbance at 450 nm between VIIa added to cells, or VIIa added to wells not containing cells. The reading was lower than the readings obtained with lowest concentration of factor Xa or thrombin and represents VIIa chromogenic activity.

Example 9 cDNA microarray. Quiescent fibroblasts were exposed to a control serum-free medium or the serum-free medium supplemented with VIIa (5 µg/ml) for 90 min (three T-75 flasks for each treatment). After the treatment, total RNA was harvested and poly (A) RNA was isolated. Six hundred ng of mRNA was labeled with either Cy3 or Cy5 fluorescence and then hybridized to the UniGem Human V chip containing 8,000 sequence verified ESTs, representing up to 5,000 known human genes (service performed by Genome System Inc for a fee). The control plate, in which known concentrations of reference cDNA was spiked into the probe generation reaction to measure sensitivity and monitor the reverse transcription reaction, purification determine hybridization efficiency and overall view of the quality and performance of the assay indicated the success of hybridization process. Global analysis of experimental data revealed minimal differences in hybridization signals between the control and VII-treated samples—Only a small number of genes showed moderate differential expression. We found upregulation of 5 genes (3.5 to 2-fold higher in VIIa treatment) whereas one gene was down-regulated upon VIIa treatment (2.4-fold lower) (+/−2 is a conservative estimate for determining the minimum magnitude of real ratios). The identity of the 3.5-fold upregulated gene was not revealed due to the proprietary nature. Other VIIa-upregulated genes are Cyr61 (2.5-fold), dopamine D2 receptor (2.2-fold), EST Incyte PD 395116 (2-fold) and P2U nucleotide receptor (2-fold). It is interesting to note that CTGF, a gene belonging to the Cyr61 family, was 1.8-fold higher in VIIa-treated cells compared to control cells. The downregulated transcript in VIIa-treated cells was EST PD674714. We selected Cyr61 for further analysis.

Example 10

Confirmation of differential expression of Cyr61. To validate the data obtained in microarray, we have patiented the RNA samples from the control and VIIa-treated cells (the same RNA samples that have been used to prepare poly (A) RNA for probe generation in the microarray) to Northern blot analysis and probed with radiolabeled Cyr61 cDNA. The data show that Cyr61 cDNA probe hybridized to a single transcript (approximately 2.0 kb) of RNA isolated from the control and VIIa-treated cells. However, the intensity of hybridization signal was much higher in RNA isolated from VIIa-treated cells (FIG. 11). Quantitation of hybridization signal revealed that expression of Cyr61 was 2.8-fold higher in cells exposed to VIIa over the control treated cells.

Example 11

Kinetics of VIIa-induced expression of Cyr61. To determine the kinetics of Cyr61 expression, quiescent fibroblasts were treated for varying time periods with 5 µg/ml VIIa. Total RNA was extracted and patiented to Northern blot analysis. As shown in FIG. 12, Cyr61 expression was increased in time-dependent manner in VIIa-treated cells. The expression was peaked at about 45 min and thereafter declined to the base level in 2 to 3 h. Since it had been reported that expression of Cyr61 in mouse fibroblasts after stimulation with serum and growth factor was sustained for several hours (up to 8 to 10 h) before repression occurs, we have examined the effect of serum and PDGF on kinetics of Cyr61 expression in quiescent human fibroblasts, WI-38. As shown in FIG. 12B, Cyr61 is expressed only transiently upon stimulation with PDGF and become fully repressed 2 h after the addition of stimuli. Similar results obtained with serum-induced expression of Cyr61 (data not shown).

Example 12

Factor VIIa-dose dependent induced expression of Cyr61. To determine dose-dependency of VIIa, quiescent fibroblasts were treated with varying doses FVIIa (0.1 to 5 µg/ml) for 45 min and then total RNA samples from the cells were patiented to Northern blot analysis. As shown in FIG. 13, treatment of fibroblasts with as low as 0.1 µg/ml FVIIa was sufficient to induce the expression of Cyr61 and a plasma concentration of FVII(a) (0.5 µg/ml, 10 nM resulted in a prominent response, close to the maximal.

Example 13

Factor VIIa-catalytic activity is required for Cyr61 induction. To test whether VIIa catalytic activity is required for the induction of Cyr61, WI-38 cells were treated with VIIa and active-site inactivated FVIIa (FVIIai) for 45 min and the expression of Cyr61 was evaluated by Northern blot analysis. As shown in FIG. 14, FVIIai failed to induce the expression of Cyr61 suggesting the requirement of FVIIa proteolytic activity. In this context, it may be important to point out that FVIIai was shown to bind cell surface TF with the same or higher affinity than FVIIa. It is unlikely that VIIa-induced expression of Cyr61 in our experiments was the result of generation of down-stream coagulation factors, FXa and thrombin. By using sensitive chromogenic assays, we found no evidence for the generation of factor Xa and thrombin in our experimental system (detection sensitivity 10 pg). Further, the specific inhibitors of factor Xa and thrombin, i.e., tick anticoagulant protein and hirudin, respectively, failed to abolish VIIa-induced expression of Cyr61 (FIG. 15).

Example 14

Involvement of transcriptional mechanism for the induction of Cyr61 mMRNA steady-state levels by VIIa. To investigate whether transcription is involved in VIIa-mediated increase in Cyr61 mRNA steady-state levels, quiescent WI-38 cells were incubated with actinomycin-D (10 µg/ml) for 30 min before the addition of VIIa for 45 min. As shown in FIG. 6, actinomycin-D inhibited the stimulator effect of VIIa. This finding indicates a transcriptional mechanism for induction of Cyr61.

To investigate whether de novo protein synthesis is required for the induction of Cyr61 nRNA by VIIa, WI-38 cells were pretreated with the protein synthesis inhibitor cycloheximide before the cells were exposed to VIIa for 45 min. As shown in FIG. 6, the stimulatory effect of VIIa was not blocked by cycloheximide. In fact, cycloheximide markedly increased the VIIa-induced Cyr61 mRNA steady-state levels.

The invention claimed is:

1. A method of treating burns in a patient comprising delivering about 500 units per kg body weight/day to about 15,000 units per kg body weight/day of a purified FVIIa to the patient.

2. The method of claim 1, wherein the purified FVIIa is recombinant FVIIa.

3. The method of claim 2, wherein the amount of recombinant FVIIa administered to the patient is in the range of 15 µg/kg/day to 200 µg/kg/day.

* * * * *